(12) United States Patent
Schroit et al.

(10) Patent No.: US 10,345,310 B2
(45) Date of Patent: Jul. 9, 2019

(54) DIAGNOSTIC TEST FOR EARLY STAGE CANCER

(71) Applicant: The Board of Regents of the University of Texas System, Austin, TX (US)

(72) Inventors: Alan Schroit, Bellaire, TX (US); Adi Gazdar, Dallas, TX (US); E. Sally Ward Ober, Collage Station, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 15/177,747

(22) Filed: Jun. 9, 2016

(65) Prior Publication Data

US 2017/0146542 A1     May 25, 2017

Related U.S. Application Data

(60) Provisional application No. 62/173,252, filed on Jun. 9, 2015, provisional application No. 62/196,695, filed on Jul. 24, 2015, provisional application No. 62/209,200, filed on Aug. 24, 2015.

(51) Int. Cl.
| | | |
|---|---|---|
| *A61K 9/127* | (2006.01) | |
| *A61K 31/685* | (2006.01) | |
| *G01N 33/574* | (2006.01) | |
| *A61K 31/727* | (2006.01) | |

(52) U.S. Cl.
CPC ....... *G01N 33/57492* (2013.01); *A61K 9/127* (2013.01); *A61K 31/685* (2013.01); *A61K 31/727* (2013.01); *G01N 33/57488* (2013.01); *G01N 2405/04* (2013.01)

(58) Field of Classification Search
CPC ..... A61K 9/127; A61K 31/685; G01N 33/574
See application file for complete search history.

(56) References Cited

U.S. PATENT DOCUMENTS

| | | |
|---|---|---|
| 6,979,554 B1 | 12/2005 | Sanson et al. |
| 8,216,784 B2 | 7/2012 | Taylor et al. |
| 8,278,059 B2 | 10/2012 | Klass et al. |
| 8,617,806 B2 | 12/2013 | Fais et al. |
| 8,637,254 B2 | 1/2014 | Taylor et al. |
| 8,956,616 B2 | 2/2015 | Thorpe et al. |
| 9,186,405 B2 | 11/2015 | Rak et al. |
| 9,400,274 B2 * | 7/2016 | Swinnen ............. G01N 33/574 |
| 2009/0148460 A1 | 6/2009 | Delcayre et al. |
| 2011/0033454 A1 | 2/2011 | Thorpe et al. |
| 2013/0178383 A1 | 7/2013 | Spetzler et al. |
| 2013/0196355 A1 | 8/2013 | Fais et al. |
| 2013/0323756 A1 | 12/2013 | Tullis et al. |
| 2014/0038901 A1 | 2/2015 | Lyden et al. |
| 2015/0044695 A1 | 2/2015 | Lozupone et al. |
| 2015/0093333 A1 | 4/2015 | Yin et al. |
| 2015/0241431 A1 | 8/2015 | Schroit et al. |

FOREIGN PATENT DOCUMENTS

| | | |
|---|---|---|
| WO | WO 2006/079120 A2 | 7/2006 |
| WO | WO 2012/038525 | 3/2012 |
| WO | WO 2012/048372 A1 | 4/2012 |
| WO | WO 2012/108842 A1 | 8/2012 |
| WO | WO 2013/033459 A2 | 3/2013 |
| WO | WO 2014/116856 A1 | 7/2014 |
| WO | WO 2015/085096 A1 | 6/2015 |
| WO | WO 2015/131153 A1 | 9/2015 |

OTHER PUBLICATIONS

Coulup et al., 2012, caplus an 2012:1512912.*
Koch et al., 2014, vol. 7(6), 752-758.*
Aharon et al., "Microparticles, thrombosis and cancer," *Best Pract Res an Haematol*, 22(1):61-69, 2009.
Al-Nedawi et al., "Endothelial Expression of Autocrine VEGF Upon the Uptake of Tumor-Derived Microvesicles Containing Oncogenic EGFR", *Proc. Natl. Acad. Sci. USA*, 106(10):3794-3799, 2009.
Arraud et al., "Extracellular vesicles from blood plasma: determination of their morphology, size, phenotype and concentration," *J Thromb Haemost*, 12:614-627, 2014.
Balasubramanian et al., "Aminophospholipid asymmetry: a matter of life and death," *Annu Rev Physiol*, 65:701-734, 2003.
Beach et al., "Exosomes: an overview of biogenesis, composition and role in ovarian cancer," *J Ovarian Res*, 7:14, 2014.
Biovision, "ExoQuant™ tumor-derived exosome enrichment and quantification assay kit (biological fluids & cell media, luminometric)," https://www.biovision.com/documentation/datasheets/K1209.pdf, retrieved Oct. 11, 2017.
Birge et al. "Phosphatidylserine is a global immunosuppressive signal in efferocytosis, infectious disease, and cancer," *Cell Death Differ*, 23:962-978, 2016.
Brekken, "Lifting the veil of immune suppression and inducing immune activation through antibody-mediated blockade of phosphatidylserine signaling," Abstract &Slides from *New York Academy of Sciences*, 'Emerging Approaches to Cancer Immunotherapy,' May 21, 2015.
Brownlee et al., "A novel "salting-out" procedure for the isolation of tumor-derived exosomes," *J Immunol Methods*, 407:120-126, 2014.
Chalasani et al., "A phase I clinical trial of bavituximab and paclitaxel in patients with HER2 negative metastatic breast cancer," *Cancer Med*, 4(7):1051-1059, 2015.
Chaput et al. "The potential of exosomes in immunotherapy," *Expert Opin Biol Ther*, 5(6):737-747, 2005.
Chen et al., "Phosphatidylserine vesicles enable efficient en bloc transmission of enteroviruses," *Cell*, 160:619-630, 2015.
Chugh et al., "Systemically circulating viral and tumor-derived microRNAs in KSHV-associated malignancies," *PLOS Pathog*, 9(7):e1003484, 2013.
Coulup et al., "Multivalent dendrimeric peptides as new biomarker probes for the detection of cancer metastasis," Abstract, *23rd Rocky Mountain Regional Meeting of the American Chemical Society*, Westminster CO, Oct. 17-20, 2012.

(Continued)

*Primary Examiner* — Sun Jae Yoo
(74) *Attorney, Agent, or Firm* — Dentons US LLP

(57) ABSTRACT

Disclosed are methods of identifying tumor-derived exosomes as an early cancer diagnostic, as well as for staging, assessing progression and assessing therapy of cancer.

14 Claims, 14 Drawing Sheets
(13 of 14 Drawing Sheet(s) Filed in Color)

(56) References Cited

OTHER PUBLICATIONS

Combes et al., "In vitro generation of endothelial microparticles and possible prothrombotic activity in patients with lupus anticoagulant," *J Clin Invest*, 104(1):93-102, 1999.

Delcayre et al., "Exosome Display technology: applications to the development of new diagnostics and therapeutics," *Blood Cell Mol Dis*, 35(2):158-168, 2005.

Escrevente et al., "Interaction and uptake of exosomes by ovarian cancer cells," *BMC Cancer*, 11:108, 2011.

Fleitas et al., "Circulating endothelial cells and microparticles as prognostic markers in advanced non-small cell lung cancer," *PLOS ONE*, 7(10):e47365, 2012.

Frey and Gaipl, "The Immune Functions of Phosphatidylserine in Membranes of Dying Cells and Microvesicles", *Semin. Immunopathol*; doi 10.1007/s00281-010-0228-6, 2010.

Gerber et al., "Stimulating an Immune Response Through Bavituximab in a Phase III Lung Cancer Study (SUNRISE)", J. Clin. Oncol., 32:5s, 2014 (suppl; abstr TPS8129); corresponding poster TPS8129, May 30, 2014 at ASCO Annual Meeting, May 30-Jun. 3, 2014, Chicago IL.

Göhner et al., "A new Enzyme-Linked Sorbent Assay (ELSA) to quantify syncytiotrophoblast extracellular vesicles in biological fluids," *Am J Reprod Immunol*, 73(6):582-588, 2015.

Gong et al., "Measuring response to therapy by near-infrared imaging of tumors using a phosphatidylserine-targeting antibody fragment," *Mol Imaging*, 12(4):244-256, 2013.

Gyorgy et al., "Membrane vesicles, current state-of-the-art: emerging role of extracellular vesicles," *Cell Mol Life Sci*, 68(16):2667-2688, 2011.

Huber et al., "Human colorectal cancer cells induce T-cell death through release of proapoptotic microvesicles: role in immune escape," *Gastroenterology*, 128(7):1796-1804, 2005.

Iero et al., "Tumour-released exosomes and their implications in cancer immunity," *Cell Death Differ*, 15(1):80-88, 2008.

Im et al., "Label-free detection and molecular profiling of exosomes with a nano-plasmonic sensor," *Nature Biotechnol*, 32(5):490-495, 2014.

International Search Report and Written Opinion for PCT/US2016/036629 dated Sep. 7, 2016.

Jakobsen et al., "Exosomal proteins as potential diagnostic markers in advanced non-small cell lung carcinoma," *J Extracell Vesicles*, 4:26659, 2015.

Kanwar et al., "Microfluidic device (ExoChip) for on-chip isolation, quantification and characterization of circulating exosomes," *Lab Chip*, 14(11):1891-1900, 2014.

Keller et al., "Systemic presence and tumor-growth promoting effect of ovarian carcinoma released exosomes," *Cancer Lett*, 278(1):73-81, 2009.

Kelleher et al., "Extracellular vesicles present in human ovarian tumor microenvironments induce a phosphatidylserine-dependent arrest in the T-cell signaling cascade," *Cancer Immunol Res*, 3(11):1269-1278, 2015.

Khan et al., "Plasma-derived exosomal survivin, a plausible biomarker for early detection of prostate cancer," *PLOS ONE*, 7(1):e46737, 2012.

Koch et al., "Microvesicles as a biomarker for tumor progression versus treatment effect in radiation/temozolomide-treated glioblastoma patients," *Transl Oncol*, 7(6):752-758, 2014.

Kupcho et al., "Abstract 3505: a bioluminescent, homogeneous annexin V microplate-based method for assessment of apoptosis," *Cancer Res*, 76(Supp 14):3505, 2016.

Lea et al., "Detection of phosphatidylserine-positive exosomes as a diagnostic marker for ovarian malignancies: a proof of concept," *Oncotarget*, 8(9):14395-14407, 2017.

Lima et al., "Tumor-derived microvesicles modulate the establishment of metastatic melanoma in a phosphatidylserine-dependent manner," *Cancer Lett*, 283(2):168-175, 2009.

Lin et al., "Exosomes: novel biomarkers for clinical diagnosis," *Sci World J*, 657086, 2015.

Llorente et al., "Molecular lipidomics of exosomes released by PC-3 prostate cancer cells," *Biochim Biophys Acta*, 1831(7):1302-1309, 2013.

Logozzi et al., "High levels of exosomes expressing CD63 and caveolin-1 in plasma of melanoma patients," *PLOS ONE*, 4(4):e5219, 2009.

Mesri et al., "Endothelial cell activation by leukocyte microparticles," *J Immunol*, 161(8):4382-4387, 1998.

Morel et al., "Cellular microparticles: a disseminated storage pool of bioactive vascular effectors," *Curr Opin Hematol*, 11(3):156-164, 2004.

Muralidharan-Chari et al., "Microvesicles: mediators of extracellular communication during cancer progression," *J Cell Sci*, 123(Pt 10):1603-1611, 2010.

Nakai et al., "A novel affinity-based method for the isolation of highly purified extracellular vesicles," *Sci Rep*, 6:33935, 2016.

NCBI Reference Sequence: NP_000033.2, beta-2-glycoprotein 1 precursor [*Homo sapiens*], https://www.ncbi.nlm.nih.gov/protein/NP_000033.2, retrieved Oct. 11, 2017.

Nieuwland et al., "Microparticles and exosomes in gynecologic neoplasias," *Semin Thromb Hemost*, 36(8):925-929, 2010.

Noerholm et al., "RNA expression patterns in serum microvesicles from patient with glioblastoma multiforme and controls," *BMC Cancer*, 12:22, 2012.

Ogasawara et al., "ImmunoPET imaging of phosphatidylserine in pro-apoptotic therapy treated tumor models," *Nucl Med Biol*, 40(1):15-22, 2012.

Otzen et al., "Lactadherin binds to phosphatidylserine-containing vesicles in a two-step mechanism sensitive to vesicle size and composition," *Biochim Biophys Acta*, 1818(4):1019-1027, 2012.

Parolini et al., "Microenvironmental pH is a key factor for exosome traffic in tumor cells," *J Biol Chem*, 284(49):34211-34222, 2009.

Rabinowits et al., "Exosomal microRNA: a diagnostic marker for lung cancer," *Clin Lung Cancer* 10(1):42-46, 2009.

Revenfeld et al., "Diagnostic and prognostic potential of extracellular vesicles in peripheral blood," *Clin Ther*, 36(6):830-846, 2014.

Saludes et al., "Cyclic peptide designed from synaptotagmin I functions as molecular probe for the detection of exosomes," Abstract, 242$^{nd}$ ACS National Meeting & Exposition, Denver CO, Aug. 28-Sep. 1, 2011.

Saludes, "Exosome capture technology based on peptide-lipid interactions," Abstract, 249$^{th}$ ACS National Meeting & Exposition, Denver CO, Mar. 22-26, 2015.

Schutters et al., "Phosphatidylserine targeting for diagnosis and treatment of human diseases," *Apoptosis*, 15(9):1072-1082, 2010.

Sharma et al., "Detection of phosphatidylserine-positive exosomes for the diagnosis of early-stage malignancies," *Br J Cancer*, 2017.

Silva et al., "Vesicle-related microRNAs in plasma of nonsmall cell lung cancer patients and correlation with survival," *Eur Respir J*, 37:617-623, 2011.

Simpson et al., "Extracellular microvesicles: the need for internationally recognised nomenclature and stringent purification criteria," *J Proteomics Bioinform*, 5:2, 2012.

Smalley et al., "Isolation and identification of potential urinary microparticle biomarkers of bladder cancer," *J Proteome Res*, 7(5):2088-2096, 2008.

Stafford et al., "Highly specific PET imaging of prostate tumors in mice with an iodine-124-labeled antibody fragment that targets phosphatidylserine," *PLOS ONE*, 8(12):e84864, 2013.

Szajnik et al., "Tumor-derived microvesicles induce, expand and up-regulate biological activities of human regulatory T cells (Treg)," *PLOS ONE*, 5(7):e11469, 2010.

Tavoosidana et al., "Multiple recognition assay reveals prostasomes as promising plasma biomarkers for prostate cancer," *Proc Natl Acad Sci USA*, 108(21):8809-8814, 2011.

Taylor et al., "MicroRNA signatures of tumor-derived exosomes as diagnostic biomarkers of ovarian cancer," *Gynecol Oncol*, 110(1):13-21, 2008.

Thery et al., "Exosomes: composition, biogenesis and function," *Nat Rev Immunol*, 2(8):569-579, 2002.

Thery et al., "Isolation and characterization of exosomes from cell culture supernatants and biological fluids," *Curr Protoc Cell Biol*, Chapter 3:Unit 3.22, 2006.

(56) References Cited

OTHER PUBLICATIONS

Thery et al., "Membrane vesicles as conveyors of immune responses," *Nat Rev Immunol*, 9(8):581-593, 2009.

Thomas et al., "Exosomal proteome profiling: a potential multi-marker cellular phenotyping tool to characterize hypoxia-induced radiation resistance in breast cancer," *Proteomes*, 1(2):87-108, 2013.

Valenti et al., "Tumor-released microvesicles as vehicles of immunosuppression," *Cancer Res*, 67(7):2912-2915, 2007.

Van Doormaal et al., "Cell-derived microvesicles and cancer," *Neth J Med*, 67(7):266-673, 2009.

Wako Life Sciences, "Exosome isolation by novel affinity molecule—MagCapture™ Exosome Isolation Kit PS," 2017.

Wako Life Sciences, "MagCapture™ Exosome Isolation Kit PS," http://www.wako-chem.co.jp/english/labchem/product/life/exosome_isolation/pdf/pi.pdf, retrieved Oct. 11, 2017.

Wieckowski et al., "Tumor-derived microvesicles promote regulatory T cell expansion and induce apoptosis in tumor-reactive activated $CD^+$ T lymphocytes," *J Immunol*, 183(6):3720-3730, 2009.

Yin et al., "Phosphatidylserine-targeting antibody induces M1 macrophage polarization and promotes myeloid-derived suppressor cell differentiation," *Cancer Immunot Res*, 1(4):256-268, 2013.

Yoshioka et al., "Ultra-sensitive liquid biopsy of circulating extracellular vesicles using ExoScreen," *Nat Commun*, 5:3591, 2014.

Zaborowski et al., "Extracellular vesicles: composition, biological relevance, and methods of study," *Bioscience*, 65(8):783-797, 2015.

Zhang et al., "Exosomes and cancer: a newly described pathway of immune suppression," *Clin Cancer Res*, 17(5):959-964, 2011.

European Extended Search Report regarding European Application No. EP 16808262, dated Dec. 18, 2018.

Coulup, "Multivalent Peptides as New Biomarker Probes for the Detection of Cancer Metastasis"(2013). Undergraduate Honors Theses. 335. Available at http://scholar.colorado.edu/honr_theses/335.

Morton et al., "MARCKS-ED Peptide as a Curvature and Lipid Sensor,"ACS Chemical Biology (1):218-225, 2012.

\* cited by examiner

FIGS. 1A-B

FIGA. 2A-C

FIGS. 10A-C

DIAGNOSTIC TEST FOR EARLY STAGE CANCER

This application claims benefit of priority to U.S. Provisional Application Ser. No. 62/173,252, filed Jun. 9, 2015, U.S. Provisional Application Ser. No. 62/196,695, filed Jul. 24, 2015, and U.S. Provisional Application Ser. No. 62/209,200, filed Aug. 24, 2015, the entire contents of each application being incorporated by reference.

This invention was made with government support under grant number RP-110442-P2 awarded by the Cancer Prevention Research Institute of Texas. The government has certain rights in the invention.

BACKGROUND

1. Field

The present disclosure relates generally to the fields of medicine, oncology and cancer diagnostics. More particularly, the disclosure provides methods, compositions and kits for diagnosing various neoplastic diseases, especially at early, asymptomatic or metastatic stages. Even more particularly, it concerns diagnostic methods for the early detection of cancer by quantifying phosphatidylserine (PS)-expressing tumor-derived cancer exosomes in patient samples.

2. Description of Related Art

While established screening programs for breast, cervical and colorectal cancer can detect asymptomatic disease, most other cancers come to clinical attention only after symptom emergence. On rare exceptions, this period may still represent early-stage disease. For instance, early hematuria can be diagnostic for bladder cancer that is still in situ or stage 1 tumor. Similarly, skin cancers are often apparent to patients and family, leading to early clinical follow-up. This is not the case, however, for the majority of visceral malignancies (thoracic, abdominal, and pelvic), where most patients remain asymptomatic at potentially curable stages. Although a minority of these cases can be investigated with blood tests or superficial tissue sampling, most of these scenarios lead to costly, invasive, and potentially morbid procedures.

Additionally, the increasing use of highly sensitive imaging technologies has resulted in an epidemic of radiographic findings of unclear clinical significance. Because of this, many affected individuals face the uncertainty and psychosocial distress inherent to a "watch and wait" approach. For instance, the annual low-dose helical chest computed tomography (CT) scans performed in high-risk patient populations in the National Lung Cancer Screening Trial (NLST) were found to be "positive" in up to 40% of individuals assessed over a 2-year period. These positive screens necessitated subsequent evaluations that included diagnostic CT, PET-CT, bronchoscopy, and even thoracotomy. Ultimately, only 4% of these cases were found to have malignancies. Cystic lesions of the pancreas (that may have malignant potential) are common, and increase with age. Incidental cysts are identified in 14% of all patients and 40% of patients over the age of 70 undergoing cross-sectional imaging. With rapidly increasing use of CT and MRI technology in emergency departments and other clinical settings, these and other "incidentalomas" are becoming a major issue threatening the quality and cost-containment of healthcare delivery. Indeed, at least 8 different "incidentalomas" involving numerous organ systems (pituitary, thyroid, pulmonary, hepatic, pancreatic, adrenal, renal, and ovarian) have been described. These radiographic findings frequently lead to recommendations for additional imaging studies, contributing to escalating health care costs and patient exposure to radiation (which has doubled in the past 15 years). These clinical events have become sufficiently common and problematic that the American College of Radiology has issued multiple white papers. Moreover, considerable psychosocial distress occurs while waiting for imaging follow-up notification and with false positive findings (40% of these experiences have been described as "very scary" or "the scariest moment of my life"). Nevertheless, Americans remain eager to participate in screening and imaging opportunities: Whole-body MRI and MRA, increasingly popular in population-based research, leads to detection of unexpected findings in 68% of otherwise healthy adults requiring further imaging or surveillance. Further complicating this issue is the recent phenomenon of electronic patient portals, where patients can view results of their diagnostic studies before their physicians have an opportunity to place them in context and provide counseling.

Therefore, there remains in the art a need for new and improved methods of diagnosing cancer that will be sufficiently sensitive to detect early stage disease and metastasis with a high degree of accuracy and reliability. The identification of a highly specific biomarker for all cancers would be an important advance, particularly a circulating blood biomarker that could be obtained with minimally invasive techniques. The field would particularly benefit from simple, cost-effective and reproducible methods to detect and quantify such a pan tumor biomarker that would clearly distinguish it from normal samples. Such a biomarker would significantly shorten the time to cancer diagnosis, resulting in earlier treatment and significantly better outcomes.

SUMMARY

The present disclosure addresses the foregoing and other needs in the field by providing methods, compositions and kits for diagnosing a variety of cancers, particularly at early, asymptomatic and/or newly-metastatic stages, by detecting and/or quantifying phosphatidylserine (PS)-expressing exosomes released from tumor cells. The methods are based on the surprising findings that circulating PS-positive tumor exosomes are diagnostic for all cancers and can be detected in biological fluids obtained by minimally invasive or non-invasive techniques, particularly blood and urine. In accordance with the present disclosure, there is provided a method of detecting a cancer cell-derived exosome from a subject comprising (a) providing a sample from the subject; (b) contacting the sample with phosphatidylserine (PS) binding agent; and (c) detecting binding of said binding agent to said exosome, thereby detecting said exosome. The sample may be a fluid, such as blood, serum, plasma, sputum, urine, tears or saliva. The binding agent may be bound directly or indirectly to a support, such as paper, plastic a bead, a nanoparticle, a nanoshell, a filter, a dish, a stick, a plate, a well, or a slide. The binding agent may be bound to the support indirectly through an antibody, where such antibody may be monomeric, dimeric or tetrameric. The cancer cell may be from any cancer including but not limited to a lung cancer cell, a pancreatic cancer cell, an ovarian cancer cell, a colon cancer cell, a renal cancer cell, a liver cancer cell, a skin cancer cell, a brain cancer cell, a head and neck cancer cell, or a thyroid cancer cell. Conversely, the absence of PS-expressing liposomes will indicate that a subject does not exhibit a malignancy, i.e., is devoid of neoplasmic disease or exhibits only benign neoplasia.

The PS binding agent may be the PS-binding domain of beta-2-glycoprotein 1 (β2GP1) also known as apolipoprotein H), such as endogenous β2GP1 found in said sample, or exogenously provided β2GP1. The β2GP1 PS-binding domain may be bound to surface, such as a plate, slide or tray, or to an antibody binding site, or may be expressed as a fusion antibody constant/framework sequences, which antibody may be monomeric, dimeric or tetrameric. The PS binding agent may be an anti-PS antibody. The PS binding agent may alternatively be PKC, PLCδ, synaptotagmin, Gas6, protein S, factor VII, factor VIII, factor IX, factor X, prothrombin, MFG-E8, Akap12, Akap81, pinin, serum response factor binding protein 1 (Srfbp), Vti1b, Fibrillarin, Mylk, Prpf40a, C2cd21, Col11a2, annexin A1, annexin 5, or lactadheren. The PS binding agent may exhibit improved binding to PS in the absence of calcium, (such as β2GP1) relative to the agent's binding to PS in the presence of calcium. The sample may be made free or essentially free of available calcium or unchelated calcium, such as 90% free, 95%, 96% free, 97%, free, 98% or 99% free of calcium or unchelated calcium.

Detecting may comprise contacting the sample of step (b) with an exosome binding agent that may be the same or other phosphatidylserine binding agent than the one used in step (b), or a non-phosphatidylserine binding agent. Given that only PS-positive tumor exosomes are captured and available at this stage (after step b), the detecting agent may be an agent that binds to all exosomes regardless of their source. Examples of agents that bind to all exosomes are phosphatidylethanolamine binding agents like duramycin and heparin, exosome markers like cd9, cd63, cd81, ALIX, HSP70, or TSG101, any of the commercially available fluorescent lipophilic probes (e.g., fatty acid analogs) that integrate into hydrophobic bilayer membranes (e.g., N-NBD-phosphatidylethanolamine, N-rhodamine-phosphatidylethanolamine and octadecyl rhodamine B chloride) and lectins, particularly mannose-binding lectins such as *Galanthus nivalis lectin* (GNA). The PS binding agent may be labeled with a detectable agent, such as a radioactive isotope, a colorimetric label, a fluorescent label, a magnetic resonance label, an enzyme, an affinity ligand, or a luminescent label. Detecting may be quantitative.

In general, normal tumor-free individuals have undetectable levels of PS-exosomes in an unconcentrated sample. In contrast, patients with tumors will typically exhibit values above 100 pg/50 μL of sample in an unconcentrated sample. Thus, values greater than 50 pg/50 μL plasma (or serum) are indicative of a malignancy.

The method may further comprise obtaining said sample from the subject prior to step (a). The method may further comprise diagnosing the subject from which the sample was obtained as having cancer. The method may further comprise staging the cancer or classifying the cancer type in the subject from which the sample was obtained. The method may further comprise performing steps (a)-(c) a second time, and comparing the results from the first and second times, thereby assessing cancer progression or regression. The method may further comprise performing steps (a)-(c) a second time, wherein the subject has received a cancer therapy after the first performance of steps (a)-(c) and before the second performance of steps (a)-(c), and comparing the results from the first and second times, thereby assessing the efficacy of cancer therapy. The method may further comprise treating the subject with a cancer therapy. The subject may be a human, or a non-human mammal.

Also provided is a kit comprising (a) a phosphatidylserine (PS) binding agent; and (b) an exosome detection agent. The kit may also further comprise one or more of (c) an antibody having binding specific for said PS binding agent; (d) a detectable label, optionally bound to said exosome detection agent; (e) a support, optionally bound to said antibody; (f) a device for obtaining a blood sample from a patient; (g) a device for storing a blood sample from a patient; and/or (h) one or more reagents for performing positive and/or negative control reactions. The detectable label may be an enzyme, a fluorescent label, a luminescent label, a radioactive isotope, a colorimetric label, or an affinity tag. The detectable label may be any commonly employed agents including rhodamine, bodipy, alkaline phosphatase, horseradish peroxidase, fluorescein isothiocyanate, or biotin.

The kit may further comprise directions for performing a cancer exosome detection assay. The exosome detection agent may be selected from cd9, cd63, cd81, ALIX, HSP70, TSG101, lactadheren, an annexin, duramycin, heparin, N-NBD-phosphatidylethanolamine, N-rhodamine-phosphatidylethanolamine or octadecyl rhodamine B chloride. The PS binding agent may be PKC, PLCδ, synaptotagmin, Gas6, protein S, factor VII, factor VIII, factor IX, factor X, prothrombin, MFG-E8, Akap12, Akap81, pinin, serum response factor binding protein 1 (Srfbp), Vti1b, Fibrillarin, Mylk, Prpf40a, C2cd21, Col11a2, annexin A1, annexin 5, or lactadheren. The PS binding agent may be full-length β2GP1 (domains 1-5), or a protein construct that contains the PS binding domain (domain 5) of β2GP1. The PS binding agent may be a recombinant antibody comprising a β2GP1 PS binding domain, domain 5 alone or any combination of domains 1-4 together with domain 5.

Also provided are (1) a method of treating a patient comprising administering an anti-cancer therapy to the patient, said patient having been determined to comprise phosphatidylserine (PS) positive exosomes, and (2) a method of treating a patient comprising performing a biopsy on the patient, said patient having been determined to comprise phosphatidylserine (PS) positive exosomes. The subject may have been determined to comprise phosphatidylserine (PS) positive exosomes by a method as described above.

Yet another embodiment comprises an isolated complex comprising: (a) a phosphatidylserine (PS) positive exosome; (b) a PS-binding agent, further comprising a detectable label bound to the complex of (a) and (b). The exosome may be an exosome isolated from a human subject. The detectable label may be bound to anti PS-binding agent antibody. The PS-binding agent may comprise the β2GP1 PS-binding domain. The PS-binding agent may be human β2GP1. The antibody may be a non-human antibody. The antibody may be a β2GP1-binding antibody. The detectable label may be bound to an exosome-binding antibody. The PS-binding agent/antibody may be bound to a solid support. The detectable label may be an enzyme, a fluorescent label, a luminescent label, a radioactive isotope, a colorimetric label, or an affinity tag. The detectable label may be rhodamine, bodipy, alkaline phosphatase, horseradish peroxidase, fluorescein isothiocyanate, or biotin. The isolated complex may alternatively comprise (a) a phosphatidylserine (PS) positive exosome; (b) a PS-binding agent; and (c) a non-human antibody that binds said exosome or said PS-binding agent.

Also provided is an isolated complex comprising (a) a phosphatidylserine (PS) positive exosome; (b) a PS-binding agent; and (c) a non-human antibody that binds said exosome or said PS-binding agent. The exosome may be an exosome isolated from a human subject. The PS-binding agent may comprise a β2GP1 PS-binding domain. The PS-binding agent may be human β2GP1. The antibody may be a non-human antibody, and/or the antibody may be a β2GP1-binding antibody. The PS-binding agent is bound to a solid support. The antibody may be bound to a solid support.

Other objects and features of the present disclosure will become apparent from the following detailed description. It should be understood, however, that the description and the specific examples, while indicating particular embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

The U.S. patent or application file contains at least one drawing executed in color. Copies of the U.S. patent or patent application publication with color drawing(s) will be provided by the office by request and payment of the necessary fees.

(FIG. 1A) Supernatants from cultured ovarian carcinoma cells (green) and mesothelial cells isolated from the same patient (red) were collected by ultracentrifugation. The pelleted exosomes were resuspended in PBS and coupled to aldehyde-activated latex beads. The beads were then incubated with FITC annexin 5 in $Ca^{2+}$-containing buffer and analyzed by FACS. (FIG. 1B) PS-positive breast carcinoma exosomes from in vitro cultured mouse 4T1 cells (green) were incubated with phospholipase C (red) to hydrolyze PS. The exosomes were then coupled to latex beads and incubated with FITC-annexin 5 as described for FIG. 1A and analyzed by FACS. The negative control (black) are beads incubated with BSA followed with FITC-annexin 5.

FIGS. 10A-C. Assessment of tumor exosomes in ovarian carcinoma patients. (FIG. 10B) ELISA assay: Tumor exosome levels in plasma from the SAME patients' with malignant disease pre (red) and 6 months post-therapy (green). (FIG. 10C) FACS assay: Same individuals shown in FIG. 10B. Thus, benign disease samples are comparable to normal samples and can be distinguished from malignant disease.

Capture was done with 1N11-T in the absence of exogenously-added human β2GP1.

Figure 13:
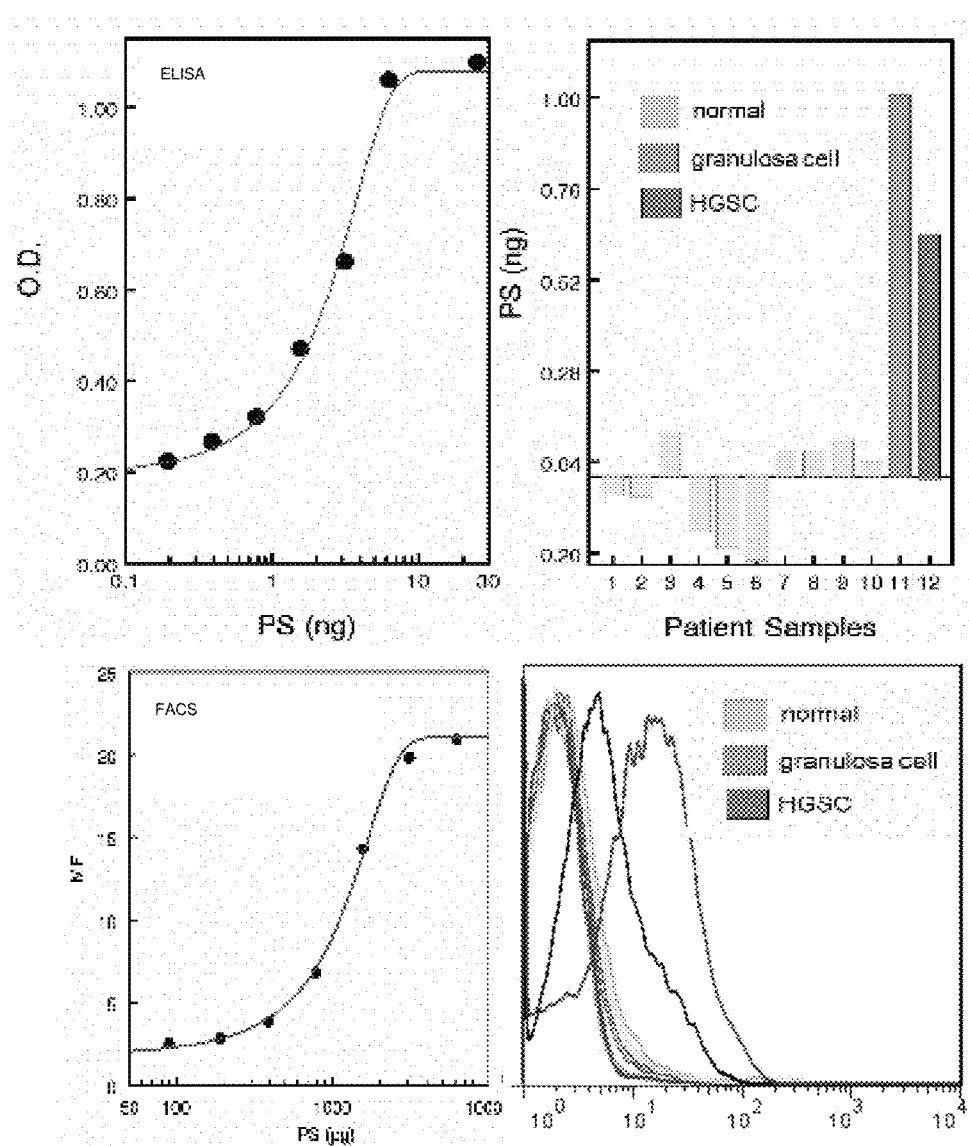

FIG. 13. Tumor exosome in normal, tumor-free individuals. ELISA (top) and FACS (bottom) analysis for tumor exosomes in the blood of tumor-free individuals (green) compared to two ovarian carcinoma patients (red and black). Left plots are standard curves obtained from PS-containing vesicles (LUV) containing 50 mol % PS in PC. Data from the ELISA and FACS assays were obtained from the same individuals. Capture with KL5C.

Figure 14:
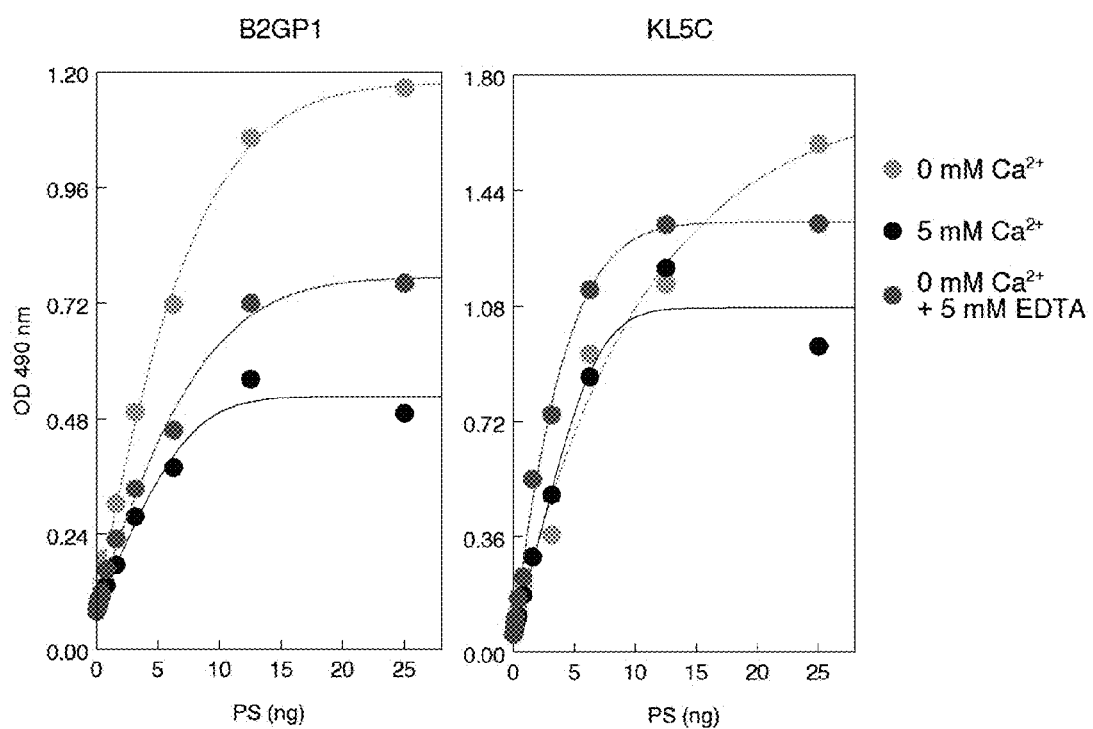

FIG. 14. Effect of Calcium on β2GP1-dependent binding to PS. ELISA plates coated with the PS capture agents β2GP1 or KL5C were incubated with increasing amounts of PS/PC LUV (mol/mol) in $Ca^{2+}$ free buffer, buffer containing 5 mM $CaCl_2$ or buffer containing 5 mM $CaCl_2$ and 5 mM EDTA.

DESCRIPTION OF ILLUSTRATIVE EMBODIMENTS

As discussed above, there is a need for new, sensitive, early detection methods for cancer, and for monitoring their progression, and assessing treatment efficacy. The data presented here indicate that phosphatidylserine (PS) constitutes a unique signature of tumor exosomes. This raises the possibility that an assay system that probes for PS exosomes in samples such as blood can be used as a surrogate indicator for malignancies in asymptomatic and symptomatic patients. In principle, this could be achieved by developing an assay system that employs PS-specific capture technologies, and a variety of secondary detection technologies for captured exosomes. Based on the data presented, such a system should specifically capture PS-expressing exosomes released from tumor cells, but would be transparent to "normal" exosomes released from non-tumorigenic cells. These and other aspects of the disclosure are presented in detail below.

I. Definitions

The phrases "isolated" or "biologically pure" refer to material which is substantially or essentially free from components which normally accompany the material as it is found in its native state. Thus, isolated peptides in accordance with the disclosure preferably do not contain materials normally associated with the peptides in their in situ environment.

"Abnormal cell" is any cell that is considered to have a characteristic that is atypical for that cell type, including atypical growth, typical growth in an atypical location or typical action against an atypical target. Such cells include cancer cells, benign hyperplastic or dysplastic cells, inflammatory cells or autoimmune cells.

As used herein the specification, "a" or "an" may mean one, or more than one, or at least one. As used herein "another" may mean at least a second or more.

The term "exosomes," as used herein, refers to a membranous particle having a diameter (or largest dimension where the particles is not spheroid) of between about 10 nm to about 5000 nm, more typically between 30 nm and 1000 nm, and most typically between about 50 nm and 200 nm, wherein at least part of the membrane of the exosomes is directly obtained from a cell membrane. Most commonly, exosomes will have a size (average diameter) that is up to 5% of the size of the donor cell. Therefore, especially contemplated exosomes include those that are shed from a cell. Platelets or their secreted particles are specifically excluded from this definition of exosomes.

As used herein, the term "sample" refers to any sample suitable for the methods provided by the present embodiments. The sample may be any sample that includes exosomes suitable for detection or isolation. Sources of samples include blood, bone marrow, pleural fluid, peritoneal fluid, cerebrospinal fluid, urine, saliva, amniotic fluid, ascites, broncho-alveolar lavage fluid, synovial fluid, breast milk, sweat, tears, joint fluid, and bronchial washes. In one aspect, the sample is a blood sample, including, for example, whole blood or any fraction or component thereof including serum and plasma. A blood sample suitable for use with the present disclosure may be extracted from any source known that includes blood cells or components thereof, such as venous, arterial, peripheral, tissue, cord, and the like. For example, a sample may be obtained and processed using well-known and routine clinical methods (e.g., procedures for drawing and processing whole blood). In one aspect, an exemplary sample may be peripheral blood drawn from a subject with cancer. In another embodiment, the sample may be platelet-free plasma.

II. Exosomes
 A. Overview

The last decade has seen an exponential growth in the number of studies and publications related to extracellular microvesicles such as exosomes. These studies range from methods for their isolation to the role of certain extracellular microvesicles, particularly exosomes, in cancer and their ability to mediate immune responses. Release of extracellular microvesicles occurs in both prokaryotes and eukaryotes and is important in a broad range of physiological and pathological processes.

Extracellular microvesicles are cell-derived and cell-secreted microvesicles which, as a class, include exosomes, exosome-like vesicles, ectosomes (which result from budding of vesicles directly from the plasma membrane), microparticles, microvesicles, shedding microvesicles (SMVs), nanoparticles and even (large) apoptotic blebs or bodies (resulting from cell death) or membrane particles, because such terms have been used interchangeably in the field (Gy6rgy et al., 2011; Simpson & Mathivanan, 2012).

"Extracellular microvesicles," as used herein, include extracellular microvesicles referred to by terminologies used for naming in the past, including terms based on the sample source from which the extracellular microvesicles were derived. As applied to tumor exosomes in particular, the terms texosomes (tex) and oncosomes have been used and are included herein, as well as terms that reflect the particular type of cancer cell, such as prostate cancer cell-derived exosomes being termed prostasomes. In addition, exosomes isolated from dendritic cells have been termed dexosomes, and other nomenclatures have been used, such as epididimosomes, argosomes, promininosomes, prostasomes and archeosomes (Simpson & Mathivanan, 2012).

Although older terminologies are included herein, it is nonetheless advantageous to define "extracellular microvesicles" using more standardized nomenclature. Naming of extracellular microvesicles considers three known mechanisms by which membrane vesicles are released into the extracellular microenvironment: exocytic fusion of multivesicular bodies, resulting in "exosomes"; budding of vesicles directly from the plasma membrane, resulting in "ectosomes"; and cell death, leading to "apoptotic blebs." The present disclosure particularly relates to the detection of "exosomes" and their use in diagnosis of cancer.

As used herein, the terms "microvesicles" and "MVs" typically mean larger extracellular membrane vesicles or structures surrounded by a phospholipid bilayer that are about 100 nm to about 1,000 nm in diameter, or about 100 nm to about 400 nm in blood plasma. Microvesicles/MVs are formed by regulated release by budding or blebbing of the plasma membrane.

"Exosome-like vesicles," which have a common origin with exosomes, are typically described as having size and sedimentation properties that distinguish them from exosomes and, particularly, as lacking lipid raft microdomains. "Ectosomes", as used herein, are typically neutrophil- or monocyte-derived microvesicles.

"Membrane particles" (MPs), as used herein, are typically about 50-80 nm in diameter and originate from the plasma membrane. "Extracellular membraneous structures" also include linear or folded membrane fragments, e.g., from necrotic death, as well as membranous structures from other cellular sources, including secreted lysosomes and nanotubes.

As used herein, "apoptotic blebs or bodies" are typically about 1 to 5 μm in diameter and are released as blebs of cells undergoing apoptosis, i.e., diseased, unwanted and/or aberrant cells. They are characterized by PS externalization and may contain fragmented DNA.

Within the class of extracellular microvesicles, important components are "exosomes" themselves, which are described as between about 40 to 50 nm and about 200 nm in diameter and being membranous vesicles, i.e., vesicles surrounded by a phospholipid bilayer, of endocytic origin, which result from exocytic fusion, or "exocytosis" of multivesicular bodies (MVBs) (GyCirgy et al., 2011; Simpson & Mathivanan, 2012). Less common, but included terms are also "vesiculation" and "trogocytosis". In some accepted definitions, exosomes can be between about 40 to 50 nm up to about 200 nm in diameter, such as being from 60 nm to 180 nm. The exosomes to be detected using the present disclosure therefore have a diameter of between about 40 nm and about 200 nm, particularly of between about 40 nm and about 100 nm or between about 50 nm and about 100 nm.

Exosomes exert a broad array of important physiological functions, e.g., by acting as molecular messengers that traffic information between different cell types. For example, exosomes deliver proteins, lipids and soluble factors including RNA and microRNAs (Thery et al., 2009) which, depending on their source, participate in signaling pathways that can influence apoptosis (Andreola et al., 2002; Huber et al., 2005; Kim et al., 2005), metastasis (Parolini et al., 2009), angiogenesis (Kim et al., 2005; Iero et al., 2008), tumor progression (Keller et al., 2009; Thery et al., 2002), thrombosis (Aharon & Brenner, 2009; Al Nedawi et al., 2005) and immunity by directing T cells towards immune activation (Andre et al., 2004; Chaput et al., 2005) or immune suppression (Szajnik et al., 2010; Valenti et al., 2007; Wieckowski et al., 2009).

Exosomes incorporate a wide range of cytosolic and membrane components that reflect the properties of the parent cell. Therefore, the terminology applied to the originating cell can be used as a simple reference for the secreted exosomes. Accordingly, "tumor-derived exosomes" can be more simply termed, "tumor exosomes," which term is widely used herein to indicate exosomes secreted by, derived from and indicative of, tumor, cancer and/or malignant cells. Similarly, "normal exosomes" are exosomes secreted by, derived from and indicative of, normal cells. In the present context, "normal cells" are substantially healthy, non-diseased, non-apoptotic and non-stressed cells; particularly as used herein, "normal cells" are non-tumorigenic cells.

Because of the multiple intracellular fusion events involved in exosome formation, the luminal contents and proteomic and phospholipid profile of the extracellularly released vesicles mirrors that of the originating cell. The presence of cytosolic (nucleic acids) and plasma membrane constituents (proteins and phospholipids) from the originating cell provides a readily accessible surrogate that reflects the properties of the parent cell for biomarker analysis. Indeed, proteomic and nucleic acid profiling of exosomes isolated from blood have identified a repertoire of moieties and oncogenic signatures specific to the cell of origin (TABLE 1).

TABLE 1

TUMOR-SPECIFIC MARKERS IN
TUMOR-DERIVED EXOSOMES

| Tumor | Tumor cell moiety in secreted exosomes | Reference |
| --- | --- | --- |
| Ovarian | ADAM10. CD9, beta 1, miRNA | (1, 2) |
| Melanoma | Caveolin 1. VLA-4. HSP70, HSP90, MET. | (3, 4) |
| Breast | HER2, miRNA | (5, 6) |
| Prostate | Survivan, FASN, XPO1 and ENO1, miRNA | (6-8) |
| Bladder | GsGTP binding protein, resistin, | (9) |
| Lung | miRNA | (10, 11) |
| Glioblatoma | Multiple up- and down-regulated RNA | (12) |

As exosome surface membranes reflect the plasma membrane of their parent cells, exosomes from tumor cells are characterized by having phosphatidylserine (PS) on their surface, as opposed to exosomes from normal cells. The methods of the present disclosure can therefore be applied used in detecting tumor exosomes that have PS exposed on their surface. In certain embodiments, the disclosure may in particular describe detection of tumor exosomes in which the PS exposed on their surface is present in association and/or approximation, or in operative association and/or close approximation, with non-lipid membrane components, particularly in association and/or approximation, or in operative association and/or close approximation, with membrane proteins. As described in detail herein, such tumor exosomes typically contain a significant amount of PS on their surface.

As discussed above, exosomes are 40-200 nm microvesicles of endocytic origin that are constitutively released by all somatic cells into the extracellular space. They are biologically active molecular shuttles that play critical roles in intracellular communication to influence many physiological and pathological processes. Depending on cellular origin, these functions include involvement in intercellular viral spread, mediation of adaptive immune responses to pathogens and tumors, and transfer of oncogenes between cancer cells and the tumor stroma that primes the so-called "metastatic niche" for metastatic spread.

In current tests for cancer, however, particles collected from the blood or other body fluids must be assessed for specific proteomic and/or genomic alterations. These assays employ extraction, processing and probing for DNA, RNA, miRNA or protein signatures that are consistent with known properties of cells that populate a specific tumor type. These are costly and time consuming processes and unless specific signatures are identified, conclusive diagnosis of disease is not possible. Cancer diagnoses could be greatly improved if a global pan-cancer specific biomarker of tumor exosomes were identified. So far, such a biomarker has remained elusive.

While all exosomes, whether from tumor cells or normal cells, share membrane epitopes found on the parent cell membrane, an exhaustive series of experiments revealed that, in contrast to exosomes secreted from normal cells, only tumor cell-derived exosomes express the membrane phospholipid, phosphatidylserine (PS), in the outer leaflet of the particle membrane (TABLE 2). Based on unequivocal data showing that PS is a unique signature of tumor exosomes, the inventors propose a biomarker-based discovery platform for the screening and detection of exosomal PS signatures in patient blood that will be diagnostic for cancer, a prognostic marker for stage of disease and a predictive marker for response to therapy and disease recurrence.

B. Exosome Isolation

Some aspects of the embodiments concern isolation of exosomes. Exosomes may be isolated from freshly collected samples or from samples that have been stored frozen or refrigerated. Although not necessary, higher purity exosomes may be obtained if fluid samples are clarified before precipitation with a volume-excluding polymer, to remove any debris from the sample. Methods of clarification include centrifugation, ultracentrifugation, filtration, ultrafiltration and precipitation. Exosomes can be isolated by numerous methods well-known in the art. One method is differential centrifugation from body fluids. Exemplary methods for isolation of exosomes are described in Losche et al. (2004); Mesri and Altieri (1998); Morel et al. (2004) and International (PCT) Publication WO/2015/085096, each of which is incorporated herein by reference. Exosomes may also be isolated via flow cytometry as described in Combes et al. (1997), incorporated herein by reference.

One accepted protocol for isolation of exosomes includes ultracentrifugation, often in combination with sucrose density gradients or sucrose cushions to float the relatively low-density exosomes. Isolation of exosomes by sequential differential centrifugations is complicated by the possibility of overlapping size distributions with other microvesicles or macromolecular complexes. Furthermore, centrifugation may provide insufficient means to separate vesicles based on their sizes. However, sequential centrifugations, when combined with sucrose gradient ultracentrifugation, can provide high enrichment of exosomes.

Isolation of exosomes based on size, using alternatives to the ultracentrifugation routes, is another option. Successful purification of exosomes using ultrafiltration procedures that are less time consuming than ultracentrifugation, and do not require use of special equipment have been reported. For example, a commercial kit is available (EXOMIR™, Bioo Scientific) which allows removal of cells, platelets, and cellular debris on one microfilter and capturing of vesicles bigger than 30 nm on a second microfilter using positive pressure to drive the fluid. HPLC-based protocols could potentially allow one to obtain highly pure exosomes, though these processes require dedicated equipment and are difficult to scale up.

Similar techniques are described in the literature, including differential/ultracentrifugation (Thery et al., 2006); affinity chromatography (Taylor & Gercel-Taylor, 2008); polymer-mediated precipitation (Taylor et al., 2011), particularly using polyethylene glycol (PEG) of different molecular weights, including the Total Exosome Isolation Reagents from Life Technologies Corporation (U.S. Pat. No. 8,901,284) and ExoQuick™ (U.S. Patent Publication 2013/0337440 A1); and capture on defined pore-size membranes (Grant et al., 2011), such as ExoMir™, which typically uses two filters of different pore-sizes connected in series (U.S. Patent Publication 2013/0052647 A1).

Improved methods of isolating and concentrating tumor exosomes were recently reported, which are based on the surprising use of acetate buffers to precipitate only PS-positive exosomes, e.g., from ascites fluid, blood, plasma and tissue culture supernatants. Such methods, which are described in U.S. Ser. No. 14/634,607 and PCT No. PCT/US15/18183, each filed Feb. 27, 2015 (each specifically incorporated herein by reference) and in Brownlee et al. (2014), provide rapid and efficient isolation procedures yielding tumor exosomes that are morphologically and antigenically indistinguishable from those obtained by ultracentrifugation. Those new methods easily accommodate very large volumes of biological material, such that the purification of tumor exosomes can be accomplished simply, without specialized equipment and at minimal cost.

"Salting-out" or "acetate methods" of isolating tumor exosomes are effective across the entire range of acetate buffers. In particular, note that "acetate buffers," by their very nature, have a pH range of between about pH 3.7 and about pH 5.8, such as having a pH range of between about pH 3.75 and about pH 5.75, or as having a pH range of between about pH 3.7 and about pH 5.6. For example, with reference to sodium acetate in particular, well-known resources such as the Buffer Reference Center of Sigma-Aldrich® show that sodium acetate-acetic acid buffer solutions have a useful pH range of between about pH 3.7 and about pH 5.6 (see also, Dawson, 1986).

The acetate methods are suitable for use with a range of acetate buffers, e.g., with monovalent or divalent cations, such as sodium acetate, potassium acetate and ammonium acetate, and mixtures thereof, with sodium acetate and potassium acetate being particular examples, and sodium acetate being particularly contemplated. Those other acetate buffers, such as potassium acetate and ammonium acetate, are also in the general pH of between about pH 3.7 and about pH 5.8, such as having a pH range of between about pH 3.75 and about pH 5.75, or as having a pH range of between about pH 3.7 and about pH 5.6.

The acetate methods also include the use of acetate buffers at a concentration of about about 0.05M, 0.06M, 0.07M, 0.08M, 0.09M or 0.10 M pH ranges of between about pH 4.14 and about pH 5.25, between about pH 4.14 and about pH 5.0, between about pH 4.39 and about pH 5.4, between about pH 4.39 and about pH 5.25 and between about pH 4.39 and about pH 5.14, and concentrations of between about 0.05M and 0.25M, between about 0.05M and 0.233M and between about 0.05M and 0.15M, are specifically contemplated; and pH ranges of between about pH 4.5 and about pH 5.4, between about pH 4.5 and about pH 5.25 and between about pH 4.5 and about pH 5.0, and concentrations of between about 0.05M and 0.233M, between about 0.05M and 0.15M and between about 0.05M and 0. 1 M are particularly contemplated.

Even more particular ranges are therefore between about pH 4.5 and about pH 5.25, or between about pH 4.5 and about pH 5.0, and concentrations of between about 0.05M and 0.15M, or between about 0.05M and 0.1M.

In certain embodiments, the acetate buffers will be essentially free from volume excluding polymers, such polyethylene glycol (PEG); dextrans such as dextran sulfate and dextran acetate; and hydrophilic polymers such as polyvinyl alcohol, polyvinyl acetate or polyvinyl sulfate.

In the acetate methods, a biological fluid sample is contacted with an acetate buffer to form a precipitate, which precipitate contains exosomes, in this case tumor exosomes, and the precipitate is collected, for example by low-speed centrifugation. If desired, the isolated opulation of tumor exosomes can be further centrifuged to remove any contaminating components, thereby providing an essentially pure composition of tumor exosomes. The isolated tumor exosomes may be washed to remove residual media and may be further "resolubilized" upon resuspension in acetate-free buffer at about neutral pH, physiological pH (such as about pH 7.35 to 7.45) and/or any standard laboratory pH, such as about pH 7.5 or 7.6 or so.

The acetate methods are able to recover a substantial amount of tumor exosomes from biological fluids such as culture supernatants, for example, being able to recover at least about half of the tumor exosomes from a culture supernatant, up to and including recovering essentially all of the tumor as exosomes from culture supernatants.

An important aspect of the acetate methods is the specificity for precipitating tumor exosomes, as opposed to exosomes from normal cells and fluids. This has significance for both practical laboratory studies and for diagnostic tests and kits, including as a first step as part of the diagnostic methods of the present disclosure. The specificity of the acetate methods leads to a number of embodiments where particular populations of tumor exosomes are prepared free or "substantially free" from other components, such as 90% free, 95% free, 96% free, 97% free, 98% free or 99% free. In particular, tumor exosomes substantially free from non-tumor exosomes, e.g., from normal cells and from non-exosome components or contaminants; and fluids such as serum substantially free from tumor exosomes.

Calcium removal may be important in certain embodiments of the disclosed methods. Ethylenediaminetetraacetic acid (or EDTA) is often provided as a disodium or potassium salt, is an effective chelating agent which binds the calcium which is needed for coagulation. It is effective at a final concentration of 1 to 2 mg/mL of blood, whereas more than 2 mg/mL causes shrinkage of the cells. Sodium citrate also chelates calcium, and is used at 3.2 to 3.8 g/dL. In ratiometric term, it can be used a 1:9, where 9 parts are blood and 1 part is sodium citrate.

III. Assay Binding Agents

The present disclosure relates to assays for detecting cancer exosomes. These assays depend on a variety of binding agents, including agents that selectively or specifically bind phosphatidylserine (PS), and that bind to other exosome markers, whether those are unique to cancer exosomes or not. The following is a general, non-limiting discussion of these agents.

A. Antibody-Based Phosphatidylserine Binding Agents

The present disclosure concerns the production and use of antibodies that bind to PS, or to a binding agent that in turn binds to PS. Antibodies are capable of "specific binding" to a particular target or series of antigenically related targets. As used herein, an antibody is said to be capable of "specific binding" to an antigen if it discriminates from antigenically distinct molecules based on binding of those molecules to the variable region of the antibody. Such interactions are in contrast to non-specific binding that involve classes of compounds, irrespective of their chemical structure (such as the binding of proteins to nitrocellulose, etc.). In particular, an antibody of the present disclosure can exhibit "highly specific binding" such that they will be incapable or substantially incapable of binding to even closely related molecules.

Monoclonal antibodies can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present disclosure) in a manner sufficient to provide an immune response. Rodents such as mice and rats are particularly useful animals. Spleen cells from the immunized animal are then fused with cells of an immortal myeloma cell. Successful fusions are then screened for production of appropriate antibodies. Antibodies may also be produced through synthetic/recombinant means where CDRs/variable regions are grafted into antibody framework regions or other antibody sequences, such as Fc regions.

In one embodiment, antibody molecules will comprise fragments (such as F(ab'), Fab) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule. A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (required for binding to protein A/G) used to purify antibodies. These fragments can often be purified/immobilized using Protein L since Protein L interacts with the variable region of kappa light chains.

The recombinant antibodies of the present disclosure may also involve sequences or moieties that permit dimerization, tetramerization or multimerization. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

Recombinant antibodies also are envisioned that contain non-antibody sequences capable of binding to targets, e.g., to phosphatidylserine. For example, domain 4 or domains 4-5 of Beta-2-glycoprotein 1 (B2GP1) can be fused to antibody sequences (Fc, framework) to permit expression of B2GP1 PS binding functionality in the context of an antibody like molecule. This permits rapid and robust cell-based production as well as the use of various antibody related technologies such as protein A purification, binding to supports with anti-IgG antibodies, etc.

Antibodies of this nature are described in U.S. Pat. No. 8,956,616, incorporated by reference in its entirety. This document discloses a range of phosphatidylserine binding construct compositions, in which the constructs comprise at least a first phosphatidylserine binding protein, polypeptide or receptor operatively attached to at least a first antibody Fc region. Joining a phosphatidylserine binding protein, polypeptide or "receptor" to an "antibody" Fc region gives rise to the terms "receptorbody" and "receptorbodies," which are used herein to refer to the phosphatidylserine-binding Fc constructs of the disclosure.

The constructs or receptorbodies of the disclosure typically comprise at least a first antibody Fc region operatively attached to at least a first phosphatidylserine binding protein or polypeptide, receptor, ligand or peptide. The term "phosphatidylserine binding protein" is succinctly used herein to refer to all phosphatidylserine binding proteins, polypeptides, receptors, ligands and peptides.

Accordingly, the term "phosphatidylserine binding protein" refers to the origin of the protein, polypeptide, receptor, ligand or peptide for use in the constructs of the disclosure, notwithstanding that some constructs of the disclosure will not bind phosphatidylserine and yet will have important biological and therapeutic uses, as set forth above.

In terms of binding phosphatidylserine, the original phosphatidylserine binding proteins and the phosphatidylserine binding proteins of the resultant constructs will bind to phosphatidylserine under biologically appropriate conditions, preferably under physiological conditions. Such phosphatidylserine binding proteins may optionally bind to other anionic phospholipids, under biologically appropriate conditions, for example under physiological conditions.

In certain particular embodiments, the phosphatidylserine binding proteins of the constructs do not substantially bind to the aminophospholipid, phosphatidylethanolamine (PE). In other particular embodiments, the phosphatidylserine binding proteins of the constructs show no detectable binding to phosphatidylethanolamine.

A range of phosphatidylserine binding proteins may be used in the constructs of the disclosure. Certain exemplary phosphatidylserine binding proteins that may be used include Protein C, Protein S, Factor II (prothrombin), Factor V, Factor VII, Factor IX or Factor X.

Other exemplary phosphatidylserine binding proteins that may be used include Mer, a PS-binding scavenger receptor, $\alpha_5\beta_3$ integrin, the CR3 complement receptor, the CR4 complement receptor and the phosphatidylserine receptor, PSr (Balasubramanian and Schroit, 2003, specifically incorporated herein by reference, see Table 2 in particular).

Other exemplary phosphatidylserine binding proteins that may be used in the constructs of the disclosure are annexins, preferably annexin V, which are particularly contemplated for use in certain embodiments, such as in further conjugates, liposomes and the like. However, in certain embodiments, the present disclosure provides constructs comprising an antibody Fc region operatively attached to at least a first phosphatidylserine binding protein, wherein said phosphatidylserine binding protein is not an annexin or a phosphatidylserine binding fragment thereof, i.e., is not annexin V or a phosphatidylserine binding fragment thereof.

Particular examples of phosphatidylserine binding proteins, polypeptides and peptides for use in the constructs of the disclosure are Beta 2-glycoprotein 1 (β2-glycoprotein 1 or β2GP1) proteins, polypeptides and peptides. Joining a β2-glycoprotein I binding protein, polypeptide or peptide to an "antibody" Fc region gives rise to the terms "betabody" and "betabodies," which are used herein to refer to particular Fc-β2GP1 constructs of the disclosure.

β2GP1, previously known as apolipoprotein H, is a 50 kDa plasma glycoprotein that binds phosphatidylserine. The DNA and amino acid sequences of .beta.2GPI from various mammalian species are known, including mouse, rat, dog, cow, chimp and human β2GP1. β2GP1 has five domains, I, II, III, IV and V, and the domain structure is conserved across mammals, as represented by domains I-V of mouse and human β2GP1.

β2GP1 binds phosphatidylserine through its C terminal domain, domain V. As the lipid and phosphatidylserine binding region(s) from β2GPI domain V are known, the phosphatidylserine binding part of the constructs of the disclosure need only contain "a lipid binding region from domain V of βGP1.

B. Non-Antibody PS Binding Agents

A variety of non-antibody agents that recognize and bind phosphatidylserine have been identified. For some, their particular binding function is known: protein kinase C (PKC), PLCδ, and synaptotagmin (through $Ca^{2+}$-dependent C2 domains), Gas6, protein S, factor VII, VIII, IX, X and prothrombin (mediated by post-translationally modified γ-carboxyglutamic acid (Gla) domain) and MFG-E8 (directly binds through a $Ca^{2+}$-independent discoidin-like C2 domain). Other PS binding agents include Akap12, Akap81, pinin, serum response factor binding protein 1 (Srfbp), Vti1b, Fibrillarin, Mylk, Prpf40a, C2cd21, Col11a2, annexin A1 (through $Ca^{2+}$-dependent), annexin 5 (through $Ca^{2+}$-dependent) and lactadheren.

A particular PS binding agent is apolipoprotein H (Apo-H), also known as $\beta_2$-glycoprotein I, is a multifunctional apolipoprotein. One of its functions is to bind cardiolipin. When bound the structure of cardiolipin and Apo-H both undergo large changes in structure. Within the structure of Apo-H is a stretch of positively charged amino acids (protein sequence positions 282-287) Lys-Asn-Lys-Glu-Lys-Lys, are involved in phospholipid binding. Apo-H has a complex involvement in agglutination, it appears to alter ADP mediated agglutination of platelets. Normally Apo-H assumes an anti-coagulation activity in serum (by inhibiting coagulation factors), however changes in blood factors can result of a reversal of that activity. The protein accession no. is NP_000033.

Apo-H has five domains, I, II, III, IV and V, and the domain structure is conserved across mammals. Apo-H binds to PS through its C terminal domain, domain V, so long as domain V is not "nicked," such as by cleavage with the enzyme plasmin, at the Lys317/Thr318 cleavage site, which destroys PS binding. Any Apo-H construct comprising a non-nicked domain V may thus be used in the disclosure, including domain V alone and in conjunction with any one or more of domains IV, III, II and I, particularly domains I and V will be used, and most particularly, full length Apo-H. Most specifically dimeric, tetrameric, octameric or other multimeric forms of Apo-H may be used.

C. Non-PS Exosome Markers and Binding Agents

In addition to PS, exosomes exhibit a number of unique and non-unique markers. Some of the exosome-specific markers include biomarkers that can help distinguish the nature of the type of cancer from which the exosome originated. Some exemplary exosome biomarkers can be found above in Table 1. Global exosome biomarkers that can be detected with appropriately labeled agents include cd9, cd63, cd81, ALIX, HSP70, TSG101, duramycin and heparin.

Another approach for the detection of tumor exosomes, once isolated using PS-binding agents, involves the use of agents that bind exosomes in a non-specific fashion. These include appropriately labeled duramycin and heparin that bind with high affinity to phosphatidylethanolamine that is expressed in the outer leaflet of all exosomes.

Another approach for the detection of tumor exosomes, once isolated using PS-binding agents, involves the use of agents that bind exosomes in a non-specific fashion. One class of agents include fatty acid analogs and phospholipids, the former including BODIPYR Fatty Acids, NBD Fatty Acids, Pyrene Fatty Acids, Dansyl Undecanoic Acid, cis-Parinaric Acid, and ADIFAB Fatty Acid Indicator. Phospholipids include Phospholipids with BODIPYR Dye-Labeled Acyl Chains, BODIPYR Glycerophospholipids, Phospholipid with DPH-Labeled Acyl Chain, Phospholipids with NBD-Labeled Acyl Chains, Phospholipids with Pyrene- Labeled Acyl Chains, Phospholipids with a Fluorescent or Biotinylated Head Group, Phospholipid with a Dansyl-Labeled Head Group, Phospholipid with a Marina BlueR Dye-Labeled Head Group, Phospholipid with a Pacific Blue™ Dye-Labeled Head Group, Phospholipid with an NBD-Labeled Head Group, Phospholipid with a Fluorescein-Labeled Head Group, Phospholipid with an Oregon GreenR 488 Dye-Labeled Head Group, Phospholipid with a BODIPYR FL Dye-Labeled Head Group, Phospholipids with a Rhodamine or Texas RedR Dye-Labeled Head Group, and Phospholipids with a Biotinylated Head Group. Particular commercial products include LipidTOX™ Phospholipid and Neutral Lipid Stains for High-Content Screening, HCS LipidTOX™ Phospholipidosis Detection Reagents, HCS LipidTOX™ Neutral Lipid Stains, and HCS LipidTOX™ Phospholipidosis and Steatosis Detection Kit.

Another class of non-specific exosomes binders includes Sphingolipids, Steroids, Lipopolysaccharides and Related Probes. Sphingolipids include BODIPYR Sphingolipids, NBD Sphingolipids, VybrantR Lipid Raft Labeling Kits, and AmplexR Red Sphingomyelinase Assay Kit. Steroids include BODIPYR Cholesteryl Esters, Side Chain-Modified Cholesterol Analog, AmplexR Red Cholesterol Assay Kit, and Fluorescent Triacylglycerol. Lipopolysaccharides include Fluorescent Lipopolysaccharides, and Pro-QR Emerald 300 Lipopolysaccharide Gel Stain Kit.

Yet another class of agents that can bind exosomes are Dialkylcarbocyanine and Dialkylaminostyryl probes. Dialkylcarbocyanine probes include DiI, DiO, DiD, DiR and analogs thereof, and substituted DiI and DiO derivatives. Also useful are other non-polar and amphiphilic probes such as Amphiphilic Rhodamine, Fluorescein and Coumarin Derivatives, Octadecyl Rhodamine B, Amphiphilic Fluoresceins and Amphiphilic Coumarin. Also contemplated for use are DPH and DPH derivatives, Diphenylhexatriene (DPH), TMA-DPH, non-polar BODIPYR Probes, BODIPYR Fluorophores, BODIPYR FL C5-Ceramide, CellTrace™ BODIPYR TR Methyl Ester, Pyrene, Nile Red and Bimane Probes, non-polar Pyrene Probe, Nile Red and Bimane Azide, as well as LipidTOX™ Neutral Lipid Stains, Membrane Probes with Environment-Sensitive Spectral Shifts, Prodan and Laurdan, DapoxylR Derivative, Anilinonaphthalenesulfonate (ANS) and related derivatives, Bis-ANS and DCVJ.

D. Conjugation of Proteins to Diagnostic Labels

In one embodiment, binding agents may be linked to various detectable agents for use in diagnosis of cancer. Linking may be performed using a variety of well-known chemical reactions and agents. An exemplary hetero-bifunctional cross-linker contains two reactive groups: one reacting with primary amine group (e.g., N-hydroxysuccinimide) and the other reacting with a thiol group (e.g., pyridyldisulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is useful that a cross-linker having reasonable stability in blood or blood products will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azidosalicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,880,270 discloses aminooxy-containing linkers useful in a variety of immunodiagnostic and separative techniques.

E. Labels

Many diagnostic agents are known in the art, as are methods for their attachment to proteins, including antibodies (see, e.g., U.S. Pat. Nos. 5,021,236; 4,938,948; and 4,472,509, each incorporated herein by reference). The moieties used can be paramagnetic ions, radioactive isotopes, fluorochromes, enzymes, fluorescent and chemiluminescent agents, dyes, affinity tags and NMR- and ESR-detectable substances.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly contemplated. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention $^{211}$astatine, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, $^{123}$iodine, $^{125}$iodine, 131iodine, $^{111}$indium, $^{59}$iron, $^{32}$phosphorus, $^{186}$rhenium, $^{188}$rhenium, $^{75}$selenium, $^{35}$sulphur, $^{99m}$technicium and/or $^{90}$yttrium. $^{125}$I is often being used in certain embodiments, and $^{99m}$technicium and/or $^{111}$indium are also often desirable due to their low energy and suitability for long range detection. Radioactively labeled receptors of the present disclosure may be produced according to well-known methods in the art. For instance, receptors can be iodinated by contact with sodium and/or potassium iodide and a chemical oxidizing agent such as sodium hypochlorite, or an enzymatic oxidizing agent, such as lactoperoxidase. TcRs according to the disclosure may be labeled with $^{99m}$technetium by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes, which exist as metallic ions to antibody are diethylenetriaminepentaacetic acid (DTPA) or ethylene diaminetetracetic acid (EDTA).

Among the fluorescent labels contemplated for use as conjugates are Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

F. Arrays and Supports

In one embodiment, the assay may employ a protein microarray of PS binding agents. An array is generally defined as a surface onto which a variety of physically segregated reactants are deposited. The resulting discrete physical locations for the reactants may be referred to as "reaction sites." The surface may be a planar surface such as a glass, plastic or silicon slide, a microtiter plate, a filter, a nitrocellulose or PVDF membrane or a bead to which a variety of capture proteins are bound. In the case of a glass, plastic or silicon slide or bead, the surface can be modified to create distinct reaction sites that bind the reactants and subsequently applied samples thereby preventing them from leaving the particular reaction site, i.e., to remain physically attached to the surface and segregated from one another. Protein immobilizing agents include various polymers, polyacrylamide gels, or surface modifications with amines, aldehydes or epoxy. The surface may also be a non-planar surface, such as a plate with multiple wells, where the wells serve the purpose of segregating reactants and samples. The major advantages of arrays are to permit highly sensitive automated, standardized and high throughput assays.

Another value of using an array is the ability to multiplex reactions. Multiplex reactions in accordance with the present disclosure may be defined in a variety of ways. For example, multiple distinct PS binding agents may be employed in a single assay. In one case, each reaction site may have a distinct PS binding agent, or may have one or more combinations of PS binding agents, with the combinations being varied by concentration, content or ratio. Since patient samples may vary in quality and content, having a variety of PS binding agents or agent combinations in a single reaction is quite useful. Multiplex reactions may also involve using different concentrations of single or multiple binding agents, permitting assessment of binding constants and quantification of target exosomes in multiple patient samples. Multiplex reactions may also include those with standard controls (e.g., binding of vesicles containing known amounts of PS), simultaneously probe for cancer-specific biomarkers with cancer-specific antibodies including prostate-specific antigen (PSA) for prostate cancer, HER2 for certain types of breast cancer, and CA125 for ovarian cancer, CEA for colorectal cancer BRCA1/BRCA2 for ovarian and breast cancer and EGFR for certain types of non-small cell lung cancer.

The solid phase and ELISA-type assays of the disclosure can be automated or performed robotically, if desired, and the signal from multiple samples can be detected simultaneously. Various such assays have been used to detect and quantify exosomes, although not using such advantageous reagents as the present disclosure. For example, antibodies to CD24 and EpCAM have been used to detect exosomes in ovarian cancer with a nano-plasmonic sensor (Im et al., 2014). A microfluidic device termed 'ExoChip' has also been described, which was used for on-chip isolation, quantification and characterization of circulating exosomes from pancreatic cancer patients and healthy individuals using antibodies against the exosome biomarker, CD63 (Kanwar et al., 2014). The detection of all tumor exosomes using PS-binding constructs, in particular high-affinity or high-avidity PS-binding constructs, can thus be accomplished using such microfluidic, chip, nano-tech and other streamlined and automated assays, whilst still retaining the specificity of the disclosure.

The solid phase binding assays of the disclosure typically require operatively associating the PS-binding construct, particularly a high-affinity or high-avidity PS-binding construct, with a solid support or substrate (which has at least one surface for coating or attachment). Such solid supports or substrates include, e.g., plates, beads and fibers. In particular embodiments of the disclosure, the solid support or substrate is a multi-well plate, such as a standard 96-well plate. The solid support or substrate may be fabricated from any suitable material, such as sepharose, latex, glass, polystyrene, polyvinyl, nitrocellulose, silicon, polydimethylsiloxane (PDMS) and the like.

IV. Diagnosis of Cancer

A. Assays

The present disclosure provides methods, compositions and kits for diagnosing cancer in animals and humans. Within animals, mammals include experimental animals (mice, rats, rabbits, guinea pigs), domestic pets and animals used to directly produce (e.g., meat) or indirectly produce (e.g., milk) food for human consumption. The disclosure therefore includes diagnostics for research, veterinary and clinical uses. In addition to human diagnosis, the disclosure therefore includes the diagnosis of mice, rats, rabbits, guinea pigs and other experimental animals; and horses, dogs, cats, cows, pigs, boar, sheep, goat, buffalo, bison, llama, deer, elk and other large animals, as well as their young, including calves and lambs.

In embodiments of the present disclosure, there are provided methods of diagnosing, staging and classifying all cancers including lung cancer, head and neck cancer, breast cancer, pancreatic cancer, prostate cancer, renal cancer, bone cancer, testicular cancer, brain cancer, thyroid cancer, liver cancer, cervical cancer, ovarian cancer, gastrointestinal cancer, lymphomas, pre-neoplastic lesions in the lung, colon cancer, melanoma, and bladder cancer.

The assays will generally follow the format of (a) providing a sample; (b) contacting said sample with an agent capable of binding specifically or selectively to phosphatidylserine (PS), and (c) detecting an exosome bound to the agent. The contacting step may be active, in the sense of providing a PS binding agent, or may be passive, as in relying on an endogenous PS binding agent found in the sample.

Next, the exosome, once bound to the PS binding agent, is detected. The detection may aided by removing other components in the sample from the exosome. This can be done in a variety of ways. For example, the binding agent may be fixed, either directly or indirectly, to a support, which can be removed from the sample, and optionally washed to remove non-specifically bound material. The exosomes may be fractionated by other means unrelated to the PS binding agent, such as centrifugation, phase separation, precipitation, etc., followed by detection.

In one aspect, the PS binding agent may itself be labeled and detected once bound to the exosome. The detection may also be achieved by use of a secondary agent that binds to the exosome in a specific or non-specific fashion. The secondary agent may be labeled, or may itself be subject to capture by binding. An exosome specific agent is one that will only bind to exosomes, or may only bind to tumor-derived exosomes. Alternatively, the secondary agent may bind to any membrane feature, and in this case will rely on the tumor exosome selectivity of the initial PS binding agent. In some cases, both the primary and secondary binding agents will be PS binding agents, and in such case it is advantageous that they have distinct PS-binding sites.

Finally, once the exosomes have been detected, they may be quantified and/or characterized. For quantification, the binding of an appropriately labeled secondary binding agent may be compared to standard curves obtained from artificially-generated 100 nm unilamellar vesicles containing graded amount of PS. Alternatively, parallel reactions with known quantities of exosomes or exosome surrogates (beads, cells, etc.) may be performed. For characterization, the exosomes may be probed for biomarkers that are characteristic of particular types of cancers including those shown in Table 1.

The disclosure also provides methods, compositions and kits for monitoring the progression of a cancer in an animal, subject or patient. These entail quantifying PS-positive tumor exosomes in a first sample from the animal, subject or patient obtained at a first time-point; quantifying PS-positive tumor exosomes in at least a second sample from the animal, subject or patient obtained at a second time-point (or at least a second time-point), the second time-point occurring after the first time-point; and comparing the amount of PS-positive tumor exosomes in the first and second samples; wherein a change in the amount of exosomes from the first sample to the second sample is indicative of progression of the cancer.

The disclosure also provides methods, compositions and kits for monitoring the staging of a cancer in an animal, subject or patient. These entail quantifying PS-positive tumor exosomes in a sample from the animal, subject or patient; comparing the quantity of PS-positive tumor exosomes to a standard that reflects a given cancer stage, thereby providing the basis for predicting the stage of the cancer in the subject from which the sample was taken.

B. ELISAs for Detecting PS-Positive Tumor Exosomes

ELISAs are well known in the field of diagnostics. Exemplary embodiments of such assays are ELISAs to detect PS-positive tumor exosomes. These function effectively in diagnosing patients with cancer in blind tests, including differentiating cancer patients from patients with benign masses.

In a particular format, ELISA plates are coated with the PS-binding construct and blocked with BSA. In using a "serum-dependent" PS antibody as the PS-binding construct in the ELISA, a "serum cofactor required for PS binding" must also be present so that the serum-dependent PS antibody and the required serum cofactor can form a tight-binding complex with any PS-positive tumor exosomes in the patient sample. The serum cofactor required for PS binding may be β2GP1. This can be performed prior to application of the PS antibody to the plate, such as by mixing the serum cofactor with the antibody prior to contacting of the antibody with the surface, or subsequent to that step, by incubating the serum cofactor with the plate-bound PS antibody, or by introducing the serum cofactor directly into the patient sample prior to adding the patient sample to the plate.

After the PS-binding construct is added to the plates, purified β2GP1 may then be added. The plates are then incubated and then washed. The ELISA is then continued by the addition of the patient blood samples (serum or plasma) and binding is detected using one or more labeled PS-binding constructs (such as HRP-annexin 5 or biotinylated annexin 5, followed by HRP-avidin) or non-specific exosome detection reagents.

In adding any required serum co-factor into an existing step of the assays or ELISAs, the serum co-factor may be added at a defined amount, which is an "effective binding amount." A "defined amount" and an "effective binding amount" of the required serum co-factor is thus an amount determined to be effective, and optionally saturating or not-limiting, for the formation of bound complexes containing the serum-dependent PS antibody, the required serum co-factor and PS-positive tumor exosomes. In the assays or ELISAs, the serum-dependent PS antibody and the required serum co-factor will both be present in amounts effective to form such "bound complexes," i.e., "antibody, cofactor, tumor exosome complexes," such that both the antibody and the co-factor are not-limiting and the variable to be detected and quantified is the amount of the PS-positive tumor exosomes in the patient sample.

V. Therapeutic Methods

The assay of the present disclosure may be used to aid in early intervention in hyperplastic/dysplastic/neoplastic diseases and conditions, including cancer. Types of diseases/conditions contemplated to be treated include lung cancer, head and neck cancer, breast cancer, pancreatic cancer, prostate cancer, thyroid cancer, brain cancer, renal cancer, bone cancer, liver cancer, skin cancers including melanoma, testicular cancer, cervical cancer, ovarian cancer gastrointestinal cancer, lymphomas, colon cancer, bladder cancer and any other neoplastic diseases. Treatment will be understood to include killing cancer cells, inhibiting cell growth, inhibiting metastasis, decreasing tumor/tissue size, tumor cell burden or otherwise reversing or reducing the malignant phenotype of tumor cells. The routes of administration will vary, naturally, with the condition of the patient, type of cancer, location and nature of the lesion, and drug, and may include, e.g., intradermal, transdermal, parenteral, intravenous, intramuscular, intranasal, subcutaneous, percutaneous, intratracheal, intraperitoneal, intratumoral, perfusion, lavage, direct injection, and oral administration and formulation. Any of the formulations and routes of administration discussed with respect to the treatment or diagnosis of cancer may also be employed with respect to neoplastic diseases and conditions. Obviously, certain types of tumor will require more aggressive treatment, while at the same time, certain patients cannot tolerate more taxing protocols.

The clinician will be best suited to make such decisions based on the known efficacy and toxicity (if any) of the therapeutic formulations.

In certain embodiments, the tumor being treated may not, at least initially, be resectable. Treatments may increase the resectability of the tumor due to shrinkage at the margins or by elimination of certain particularly invasive portions. Following treatments, resection may be possible. Additional treatments subsequent to resection will serve to eliminate microscopic residual disease at the tumor site. Some common cancer therapies include chemotherapy, radiotherapy, gene therapy, immunotherapy, hormonal therapy, toxin therapy or surgery.

The disclosure further provides methods, compositions and kits for monitoring therapeutic efficacy of an anti-cancer treatment. This includes quantifying PS-positive tumor exosomes in a first sample from an animal, subject or patient obtained at a first time-point, the first time-point occurring before the cancer treatment, quantifying PS-positive tumor exosomes in at least a second sample from the animal, subject or patient obtained at a second time-point, the second time-point occurring after the cancer treatment; and comparing the amount of PS-positive tumor exosomes in the first and second samples; wherein an increased amount of exosomes in the second sample relative to the first sample is indicative of lack of therapeutic efficacy, and a decreased amount of exosomes in the second sample relative to the first sample is indicative of therapeutic efficacy. Similarly, quantifying PS-positive tumor exosomes in a third sample from an animal, subject or patient obtained after the second time point, the second time-point occurring after the cancer treatment, quantifying PS-positive tumor exosomes in at least a third sample from the animal, subject or patient obtained at a third time-point, the third time-point occurring after the cancer treatment; and comparing the amount of PS-positive tumor exosomes in the second samples; wherein a reduced amount of exosomes in the third sample relative to the second sample is indicative of continued therapeutic efficacy and disease remission, while an increased amount relative to the second sample would be indicative of disease recurrence and/or metastasis.

VI. Examples

The following examples are included to demonstrate particular embodiments of the disclosure. It should be appreciated by those of skill in the art that the techniques disclosed in the examples which follow represent techniques discovered by the inventors to function well in the practice of the disclosure, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the disclosure.

Example 1

The Distribution of PS in the Membrane of Exsomes Derived from Normal Cells and from Tumor Cells The present example, together with Table 2, show that in contrast to exosomes isolated from normal non-tumorigenic cells that do not express PS on the exosome surface membrane, exosomes isolated from tumor cells express relatively large measurable amounts of PS their membrane surface. These data suggest therefore that exosomes from normal or tumor cells can be distinguished from one another by tests that discriminate between the presence and absence of PS on the surface of exosomes.

A. Materials and Methods

Isolation of normal mesothelial cells and ovarian carcinoma cells from malignant ascites of an ovarian carcinoma patient. Ovarian tumor cell lines and mesothelial cell lines were established from 0.5 to 3.0 liters of ascites. The fluid was centrifuged and the resulting cell pellet was resuspended in medium and the tumor clusters were allowed to sediment while the mesothelial cells remained in suspension. Several cycles of differential sedimentation were employed to purify populations of carcinoma and mesothelial cells. A final step of differential plating was used to further separate mesothelial cells from the ovarian tumor clusters. Each cell type was then cryo-preserved (90% FBS, 10% DMSO) and grown in ACL4 medium.

Cell lines. Cells (~25×10$^6$ in 15 mL media) were seeded into the lower chamber of CELLine AD 1000 flasks (Integra Biosciences AG) that contained 250 mL media in the upper chamber. Conditioned media (~15 mL) was collected from the lower chamber weekly. The compartment was washed once with 15 mL of phosphate-buffered saline (PBS) that was combined with the conditioned media before adding fresh media to the lower chamber. The upper chamber was replenished weekly by replacing ~100 mL spent media with fresh media. Weekly collections typically yielded 75-125 µg of purified exosomes/mL of conditioned media.

Exosome isolation. Cell conditioned media was cleared of cells, cell debris and large membrane vesicles by sequential centrifugation at 500 g for 30 min followed by 12,000 g for an additional 30 min. Exosomes were collected from the cleared supernatants after centrifugation and one wash in HEPES-saline (NaCl 150 mM, HEPES, 20 mM, EGTA 2 mM, pH 7.6) at 70,000 g for 2 hrs. The pellets were finally resuspended in ~0.5 mL HEPES-saline. Exosome quantity was estimated by BCA protein assay.

Hydrolysis of Exosome Surface Phospholipids with Phospholipase C. Tumor exosomes (50 µg) isolated from mouse 4T1 breast carcinoma cells were resuspended in hydrolysis buffer (2 mL of Tris-saline pH 7.6 with 10 mM $CaCl_2$) and incubated for 12 hours at 20° C. The suspension was then diluted with HEPES-saline buffer to 30 mL and the exosomes were collected after centrifugation at 70,000 g for 2 hours. Phospholipase-treated exosomes were also confirmed to be PS free by thin-layer chromatography (not shown).

Flow Cytometry. Exosomes (10 µg protein) in 0.5 mL HEPES-saline were mixed overnight at 4° C. with 5 µL of 4 mM aldehyde-activate latex beads (4% w/v) (Invitrogen). The beads were then blocked with 0.5 mL of 1% bovine serum albumin (BSA) for 1 hr followed by 0.1 mL of 100 mM glycine for an additional hour. The beads were washed (5,000 g for 5 min.) and resuspended in HEPES-saline containing $Ca^{2+}$ (1 mM) and FITC-labeled annexin 5 (BD Biosciences). Samples were analyzed using a BD Biosciences FACS Calibur. Data was analyzed with FlowJo.

B. Results

Figure 1:
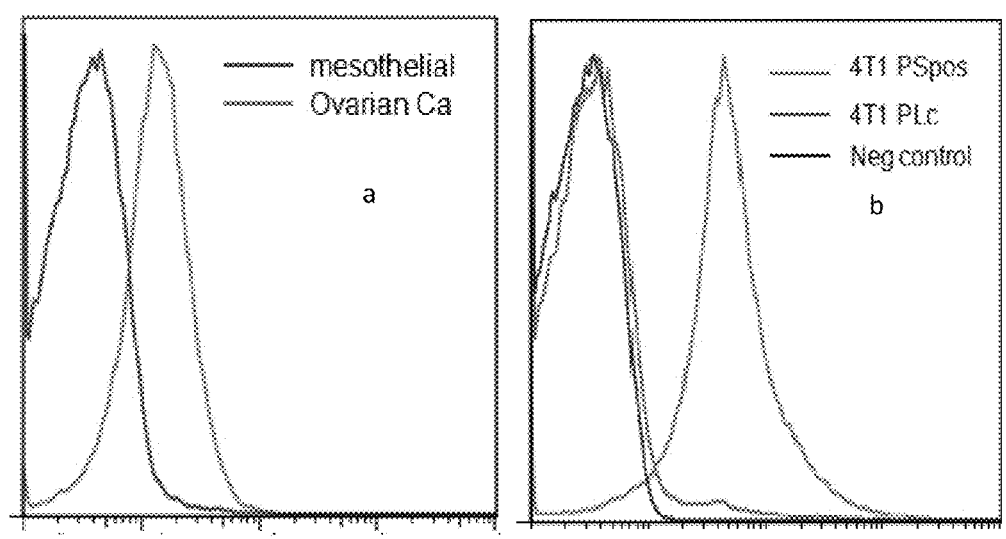
FIGS. 1A-B. Distribution of PS in exosomes derived from normal cells and tumor cells.

FIG. 1A shows FITC-annexin 5 labeling of exosomes derived from mesothelial cells (red line; normal cells) and ovarian carcinoma cells (green line; tumor cells) from malignant ascites of the same patient. The data indicate that PS cannot be detected on the surface of exosomes derived from normal mesothelial cells (red line). In contrast, exosomes derived from ovarian carcinoma cells have relatively large amounts of PS present on the exosome surface (green line). To confirm that the FITC-annexin 5 labeling of the tumor exosomes was because of the presence of PS on the surface of tumor exosomes, cell surface phospholipids were hydrolyzed to phosphatidic acid with phospholipase C. FIG. 1B shows that PS expressing tumor exosomes (green line; 4T1 breast carcinoma derived exosomes) were not labeled with FITC annexin 5 after phospholipase C hydrolysis (red line) and had values comparable to that of a negative control (black line).

Taken together, these data indicate that tumor exosomes express PS on their membrane surface whereas exosomes from normal non-tumorigenic cells do not express PS on their membrane surface. Hydrolysis of exosomal PS with phospholipase C indicated that labeling with FITC-annexin 5 was due to the presence of PS and not to other exosome membrane components.

Example 2

PS Binding Constructs

Figure 2:
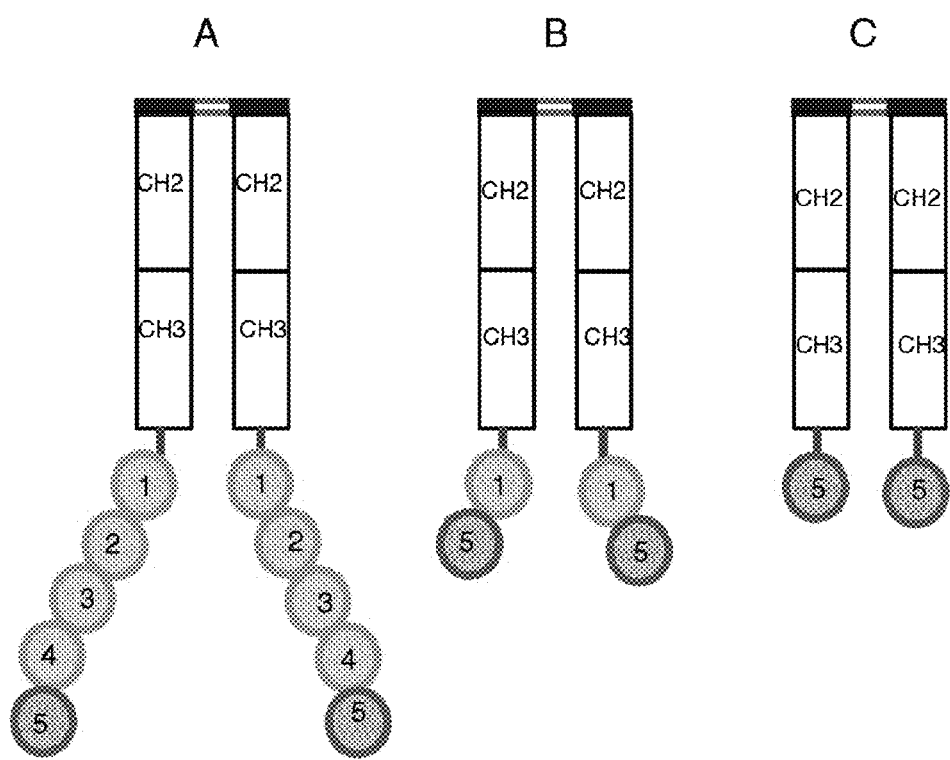
FIGS. 2A-C. Structure of exemplary dimeric betabody (β2GP1) constructs that bind PS. Betabody constructs are composed of two full or partial beta-2-glycoprotein 1 (β2GP1) polypeptides attached to the antibody Fc region that bind to PS. A betabody construct may contain all five β2GP1 domains (FIG. 2A) of which domain 5 is the PS binding domain. Other betabodies may contain domain 5 together with any other combination of domains as exemplified in FIG. 2B and FIG. 2C. The β2GP1 domains may also be coupled to the Fc N-terminus (not shown).

This example describes the design of various PS-binding constructs that selectively bind
PS-expressing tumor-derived exosomes. A series of PS binding proteins and constructs were tested as candidates for a high affinity capture moiety for use in the development of a sensitive and specific PS exosome assay. These included full-length β-2-glycoprotein 1 (β2GP1, also known as apolipoprotein H), a serum protein known to bind PS and various betabody constructs (FIGS. 2A-C).

Betabody constructs are dimeric (bivalent), PS binding proteins in which two β2GP1 polypeptides, each containing one or more domains of β2GP1, are attached to an antibody Fc region to create an antibody-like molecule. In a betabody, two β2GP1 polypeptides each containing at least the PS-binding domain 5 of β2GP1 are attached to an antibody Fc region. Optionally, the two β2GP1 polypeptides in a betabody may additionally contain other β2GP1 domains, particularly domain 1, up to including all domains 1, 2, 3, 4, and 5 (FIG. 2A and FIG. 2B) and any combination thereof. Initial betabody constructs tested include those in which two β2GP1 domain 5 are linked to an antibody Fc region at the C-terminal (FIG. 2C) and those in which two β2GP1 polypeptides containing both domain 1 and 5 (FIG. 2B) and domains 1-5 (FIG. 2A).

Certain β2GP1 binding antibodies were also included in the initial tests. In particular, the antibody termed 1N11, which is a fully human antibody that binds PS through its binding to β2GP1. In the presence of plasma that contains endogenous β2GP1 (~100 µg/mL) or purified β2GP1, 1N11 binds (indirectly) to PS.

Figure 3:
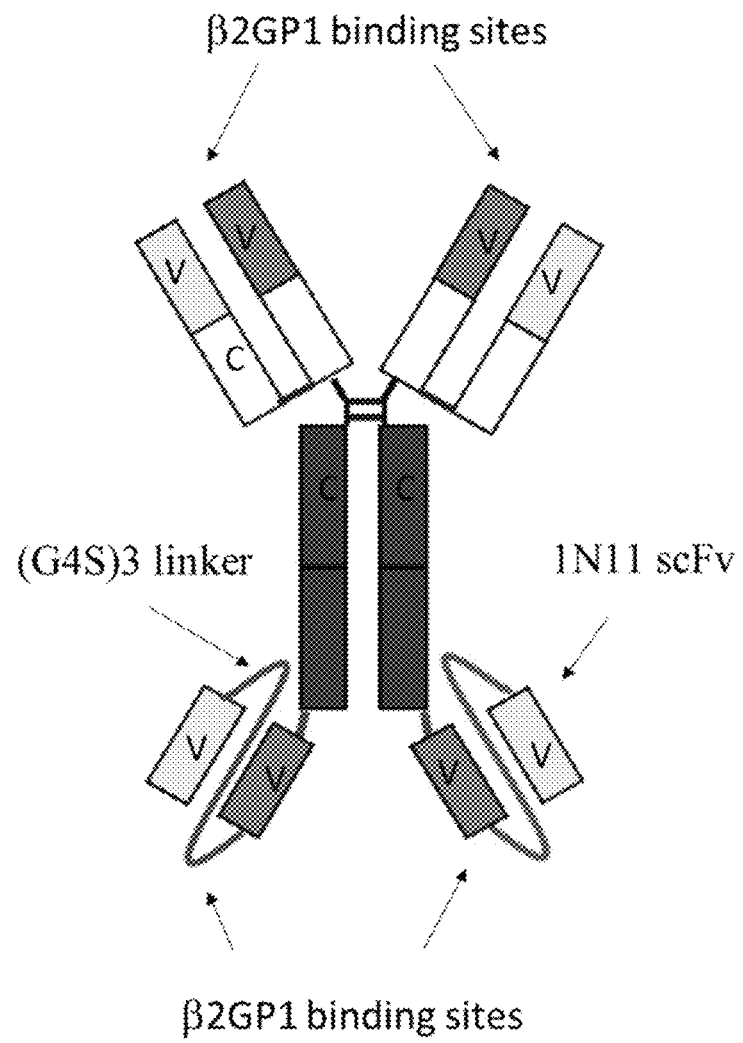
FIG. 3. Structure of 1N11 tetramer (1N11-T). Two additional β2GP1 binding sites have been added to the Fc C terminal of 1N11 antibody two create a construct with tetrameric β2GP1-dependent PS-binding sites.

Also tested was a 1N11 construct with tetrameric β2GP1 binding sites (FIG. 3). Although this construct is termed 1N11-T (tetrameric) this is not an antibody tetramer but more akin to a dimeric antibody, in which the tetrameric component comes from the two additional β2GP1 binding sites attached to the C-terminal (FIG. 3). Both 1N11 and 1N11-T require the presence of β2GP1 to effectively bind PS.

Example 3

Assays Confirming PS Binding of PS Binding Proteins and PS Binding Constructs

The data presented in FIGS. 4-7 show the propensity of the various PS binding proteins to specifically bind PS that is incorporated into the membranes of artificially-generated vesicles containing PS. The results from all four assay systems (vesicle aggregation, ELISA, FACS and array analysis) confirm that the indicated PS-binding proteins/ constructs can be used to quantify PS-expressing tumor exosomes present in patient blood.

Figure 4:
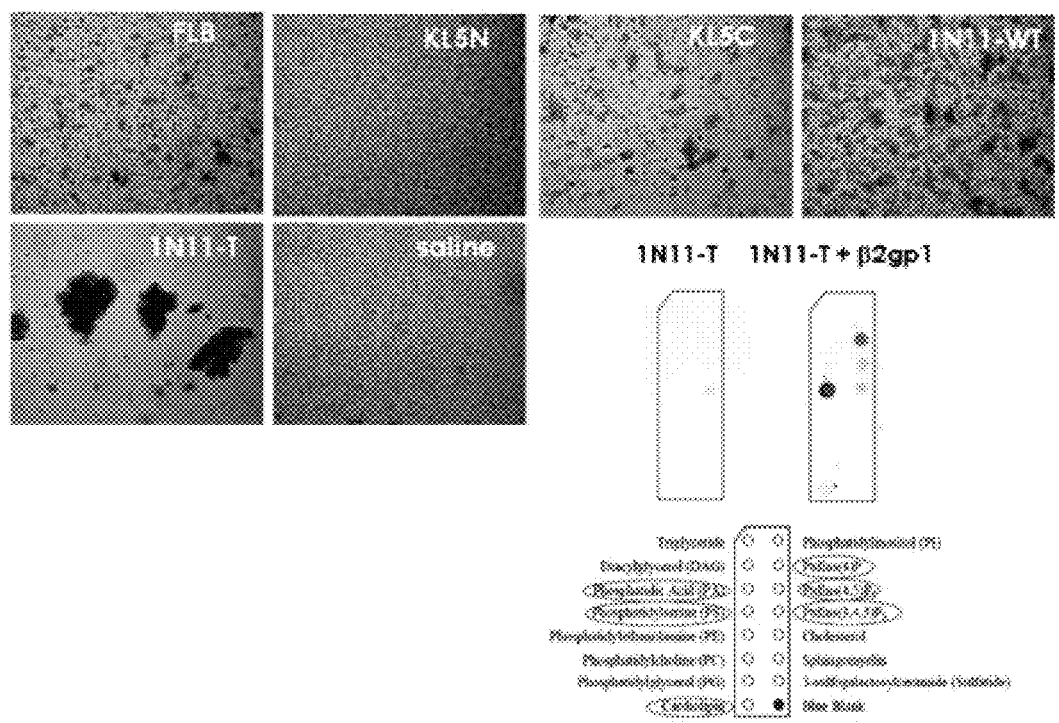
FIG. 4. Binding of PS constructs to PS-containing multilamellar (MLV) vesicles in solution. Photomicrographs: The indicated constructs/antibodies (5 µg) were mixed with PS-containing vesicles (50 µg) and immediately photographed. The extent of aggregation and the lipoblot results indicate preferential binding to PS (negatively-charged lipids are circled in red). FLB is full-length β2GP1, KL5N is a domain 5 containing betabody at the Fc N-terminal, KL5C, is a domain 5 containing betabody at the Fc C-terminal. The 1N11-WT (wild-type) antibody and tetrameric 1N11 (1N11-T) were added together with exogenous human β2GP1 (2 and 4 mol excess, respectively).

Aggregation Assay. Multilamellar vesicles containing 50 mol % PS in PC were prepared in normal saline. These vesicles (50 µg) were mixed with 5 µg of the indicated binding agents and immediately placed on glass slides and photographed at 100× magnification. The extent of aggregation is an indication of the relative binding affinity of the various proteins/constructs. FIG. 4 shows weakest binding with KLSN, an N-terminal domain 5 containing betabody, intermediate binding with FLB (purified full-length human β2GP1) and KLSC, a C-terminal domain 5 containing betabody (see FIG. 3C) and 1N11-WT, wild type divalent human anti-β2GPI (with added exogenous β2GP1). The strongest binding was obtained with 1N11-T (see FIG. 4) in the presence of exogenous β2GP1.

FIG. 4 also shows lipoblot analysis for the lipid binding specificity of 1N11-T. Briefly, the indicated lipids were deposited on nitrocellulose membranes. The membranes were then flooded with 1N11-T alone (left) or 1N11-T with added β2GP1. After washing the amount of bound antibody was determined with labeled anti human Ig. The results show that 1) binding of 1N11 is dependent on the presence of β2GP1 and 2) in the presence of β2GP1 1N11 binds well to PS and to lessor degrees to negatively-charged inositol phosphates. Red circles indicate negatively-charged lipids.

Figure 5:
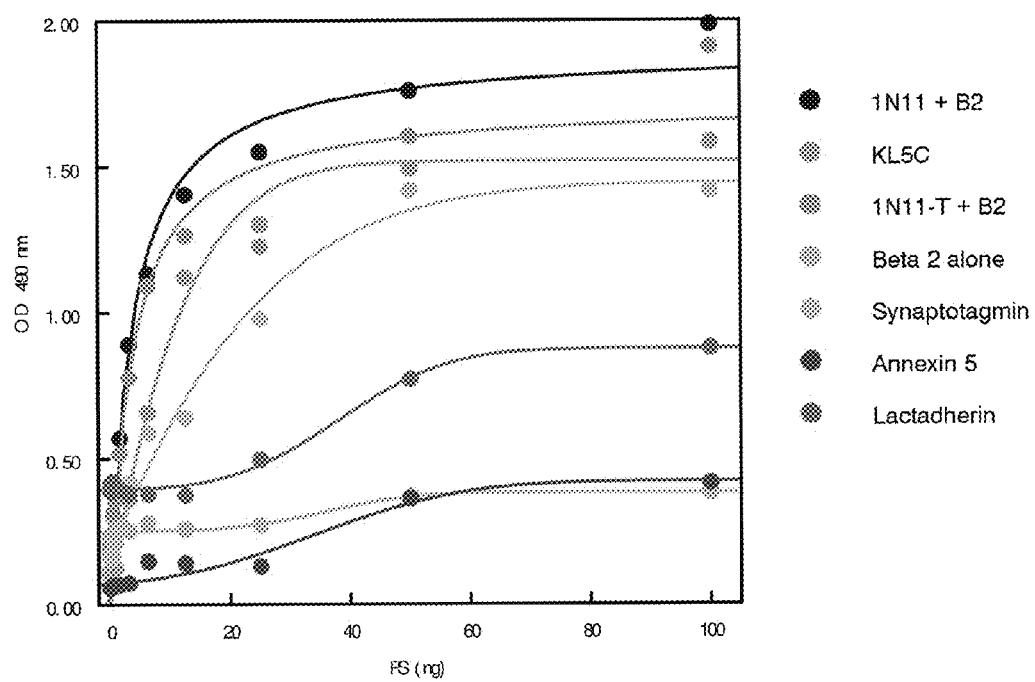
FIG. 5. Binding of PS constructs to PS-containing large unilamellar vesicles (LUV) by solid phase ELISA. ELISA plates were coated with the indicated binding agents (1 µg/well) and incubated with LUV containing the indicated amounts of PS [50 mol % in phosphatidylcholine (PC)]. With the exception of annexin 5 and synaptotagmin that were added together with Calcium (2 mM), the other binding agents were incubated in the absence of calcium. After removing unbound vesicles, the plate was developed with HRP-annexin 5 in $Ca^{2+}$-containing buffers.

ELISA assay. ELISA plates were coated with 1 µg of the indicated binding agents overnight. The following day the plates were washed and blocked for 1 hr with 2% bovine serum albumin in HEPES-saline buffer. The plates were washed again and decreasing amounts (double dilutions) of large unilamellar vesicles (LUV) containing 50 mol % PS in phosphatidylcholine were added to each well (from 100 ng of PS/50 µL/well). After 2 hour incubation the plates were washed again and HRP-annexin 5 was added for an additional 1 hour. The plates were washed again and developed. Optical density (OD) was determined at 490 nm (FIG. 5).

With the exception of annexin 5 and synaptotagmin that were incubated throughout in the presence of $Ca^{2+}$ (1 mM; both these agents require calcium for PS binding) all the other agents were incubated in $Ca^{2+}$-free buffers up to the step of adding the HRP-annexin 5.

The results show excellent binding profiles for 1N11 with added β2GP1, 1N11-T with added β2GP1, KL5c and synaptotagmin. Quantitative binding profiles were also obtained with lactadheren, annexin 5 and β2GP1 alone albeit the intensity of the readings were significantly less than those in the first group.

Taken together these data suggest that 1N11 (both wild-type and tetramer) and KLSC betabody are the agents of choice for the development of a quantitative PS binding assay for the detection of tumor-derived exosomes in patient blood.

FACS assay. To confirm the utility of 1N11-T in detecting PS-expressing exosomes FACS analysis was performed using the same parameters as employed in the ELISA assay (above). Briefly, 1N11-T (10 µg protein) in 0.5 mL HEPES-saline was mixed overnight at 4° C. with 5 µL of 4 mM aldehyde-activate latex beads (4% w/v) (Invitrogen). The beads were then blocked with 0.5 mL of 1% bovine serum albumin (BSA) for 1 hr followed by 0.1 mL of 100 mM glycine for an additional hour. The beads were washed (5,000 g for 5 min.) and resuspended in HEPES-saline containing β2GP1 and the indicated amounts of PS-containing LUV (50 mol % in phosphatidylcholine). After 1 hour incubation, the beads were washed again and FITC-annexin 5 in HEPES-saline containing CaCl$_2$ (1 mM) was added. Samples were analyzed using a BD Biosciences FACS Calibur. Data was analyzed with FlowJo.

Figure 6:
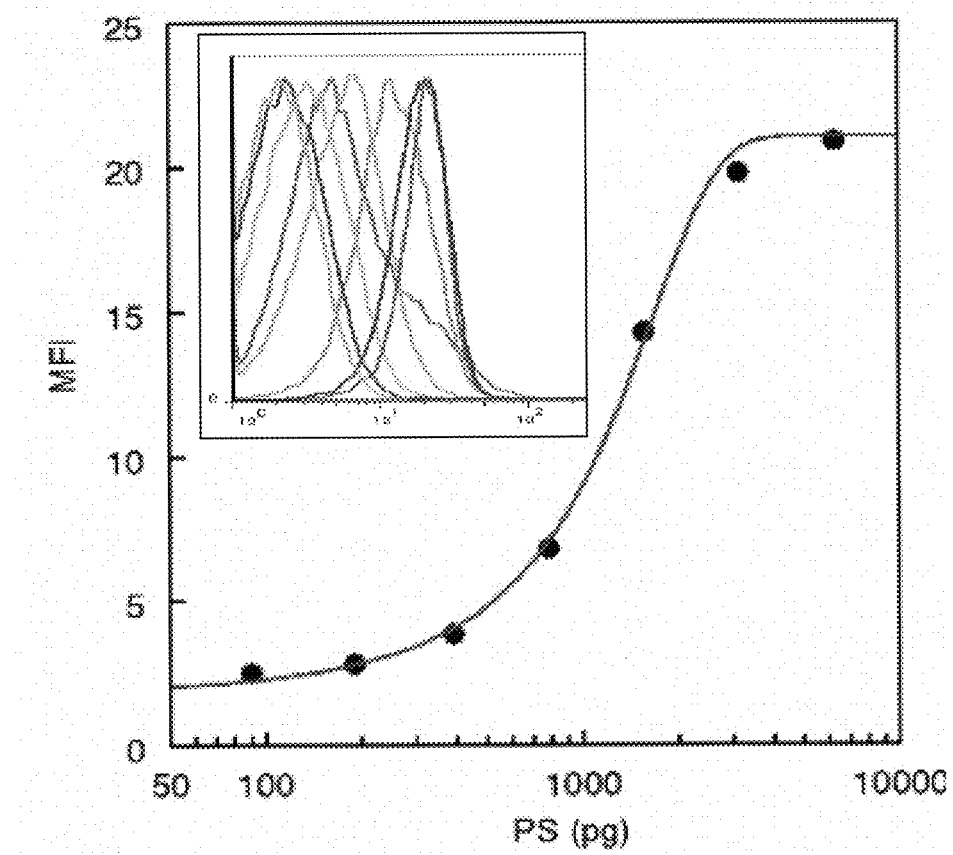
FIG. 6. Binding of 1N11-T to LUV by solid phase FACS bead assay. Aldehyde-activated latex beads were coated with 1N11-T overnight. Unreacted aldehydes were then blocked with 0.1 M glycine. The beads were then incubated for 1 hr with the indicated LUV in the presence of excess exogenously-added human β2GP1 and assessed by FACS after labeling with FITC-annexin 5. Fluorescent intensities versus amount of PS. Inset: Actual FACS plots obtained with increasing amounts of PS LUV from left to right.

FIG. 6 shows a linear relationship between the mean fluorescent intensity (MFI) of samples containing increasing amounts of PS-containing LUV. Inset shows actual FACS scans of the various LUV preparations from which the standard curve was developed.

Figure 7:
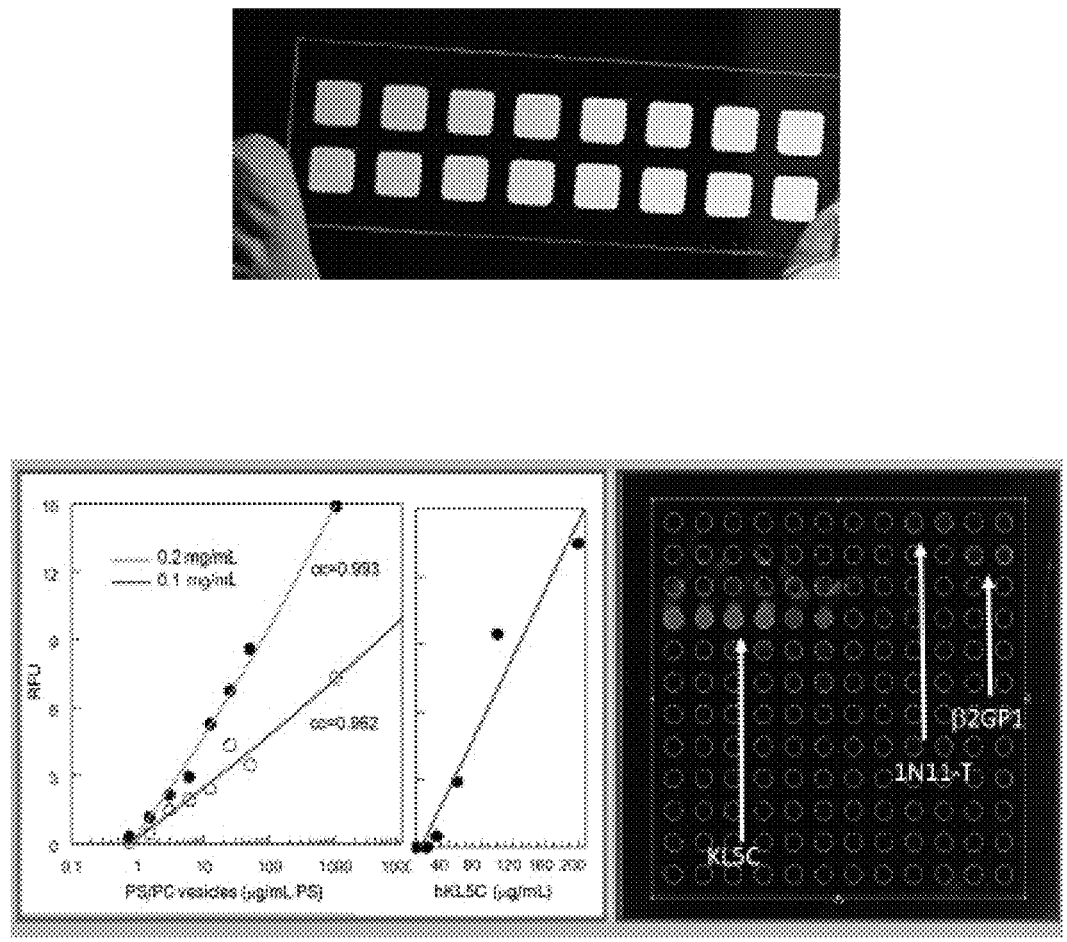
FIG. 7. Array analysis: Binding of KLSC to decreasing concentrations of LUV containing 50 mol % PS in PC. Different amounts of KLSC were plated on the array (right) and tested for the ability to detect increasing concentrations of PS containing vesicles (left). Captured vesicles were detected with CY5-labeled annexin 5. Top: Typical array slide that can simultaneously test 16 patients with >100 combinations of binding agent/antibodies/patient.

Array assay. FIG. 7 shows preliminary assessment of array detection for quantifying tumor exosomes. Briefly, the array was coated with increasing concentrations of capture agents and assessed for the ability to generate standard curves with PS-expressing vesicles. Similar to ELISA assay, capture with KLSC yielded standard curves with nearly perfect linearity (FIG. 7, left). These data suggest that, with further optimization for sensitivity and reproducibility, a multiplexed array that simultaneously detects malignancy (PS exosomes), site-specific tumor markers (e.g., CA125, HER2, etc.) and pan exosome markers (duramycin, heparin, etc.) can be developed to become the assay system of choice.

Example 4

Quantitation of PS-Expressing Tumor Exosomes in Patient Blood

While the PS binding assays are highly dependent on capture of (only) PS-expressing tumor exosomes (the presence of normal, non-PS-expressing exosomes are not detected and is transparent to the system) the quantitation step of the captured tumor exosomes can be by detection of PS using, for example, HRP-annexin 5 or biotin-annexin 5 followed by HRP-streptavidin that will also provide a secondary selection step. However, because of the high stringency obtained with the initial capture, sensitivity can be increased by using detection methods that quantify any of a number of pan exosome markers. To demonstrate this, tumor exosomes in the plasma of ovarian carcinoma patients and normal tumor-free individuals were captured on ELISA plates coated with KLSC and detected by quantifying exosomal PS with HRP-annexin 5 or phosphatidylethanolmine, a non-tumor specific pan exosomes marker, with HRP-duramycin.

A. Methods

Standard curves. Standard curves (FIG. 8, left) were generated with LUV composed of PS/PC/and phosphatidylethanolamine (PE) (1/1/1) that were captured on ELISA plates containing KL5C betabody as the selective PS capture agent. The wells were incubated with decreasing amounts of LUV (double dilutions) from 100 ng PS/well. After washing the amount of PS and PE bound to plate was determined with HRP-annexin 5 (in Ca$^{2+}$-containing buffer) and HRP-duramycin (in Ca$^{2+}$-free buffer), respectively.

Quantitation of Tumor Exosomes in Plasma from Normal Individuals and from Ovarian Carcinoma Patients. Blood (~1 mL) was collected in purple-capped EDTA vacutainers from normal individuals and ovarian carcinoma patients. The blood was immediately centrifuged at 700 g for 10 minutes and the cell-free supernatant was collected and centrifuged again at 10,0000 g to remove platelets. This platelet-poor plasma (ppp) was used in the ELISA assays. Briefly, KLSC-coated ELISA plates were incubated with 100 μL of 1/1 diluted plasma with phosphate-buffered saline. After 2 hours incubation the plates were washed and the amount of bound exosomes was determined by quantifying PS with HRP-annexin 5 or PE with HRP duramycin. The results presented in FIG. 8 (right plot) show ~5-fold increase in the number of tumor exosomes present in cancer patients compared to normal individuals when assessed with HRP-annexin 5. However, using the pan exosome marker HRP-duramycin, ~157-fold increase in the number of tumor exosomes in the cancer patient's vs normal was observed.

These data suggest the following. First, plasma from normal, tumor-free individuals contain no detectable PS-expressing tumor exosomes. Second, detection of PS-expressing tumor exosomes can be increased ~10-fold when detected with a pan exosomal marker such as duramycin instead of PS. Taken together, these data indicate that the stringency of PS-mediated tumor exosome capture is sufficiently high that highly expressed non-tumor specific exosome markers can be used to quantify selective tumor exosome capture.

Example 5

Figure 8:
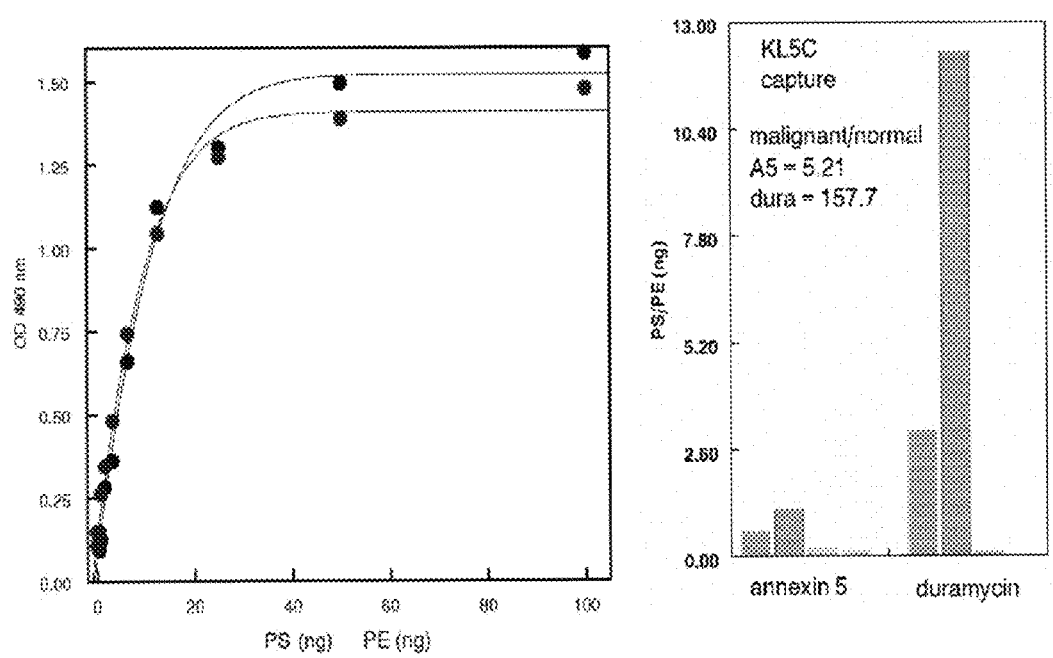
FIG. 8. ELISA assay of plasma from normal individuals and ovarian carcinoma patients-employing betabody capture and captured PS-positive exosomes quantified with HRP-annexin 5 (for PS) and HRP-duramycin (for phosphatidylethanolamine). Left: Standard curves generated with LUV composed of PC/PS/phosphatidylethanolamine (PE) (1/1/1) were captured on ELISA plates with KL5C. PS (black) and PE (blue) were individually quantified with HRP-annexin 5 and HRP-duramycin, respectively. Right: Duplicate plasma samples from two normal individuals (green) and two ovarian carcinoma patients (red) were captured on ELISA plates with KL5C and quantified with either HRP-labeled annexin 5 or HRP-duramycin. The malignant/normal capture ratio for PS and PE detection are shown.

Detection of PS-Expressing Tumor Exosomes with the Phsophatidylethanolamine (PE) Binding Agent Heparin Sulphate While heparin sulphate is commonly employed therapeutically and in blood collection as an anticoagulant, we discovered that heparin binds with high affinity to PE containing membranes. This raised the possibility that heparin can be used as non-specific pan exosome marker to detect PS-dependent tumor exosome capture, similar to duramycin as shown in FIG. 8 and EXAMPLE 4 above.

A. Method

ELISA plates were coated with 1 μg of heparin sulphate overnight. The plates where then washed and incubated with increasing amounts of LUV containing 50 mol % PE or 50 mol % PS in PC. After washing, the amount PS- and PE-containing LUV bound to the plate was determined with HRP-annexin 5 and HRP-duramycin, respectively.

B. Results

Figure 9:
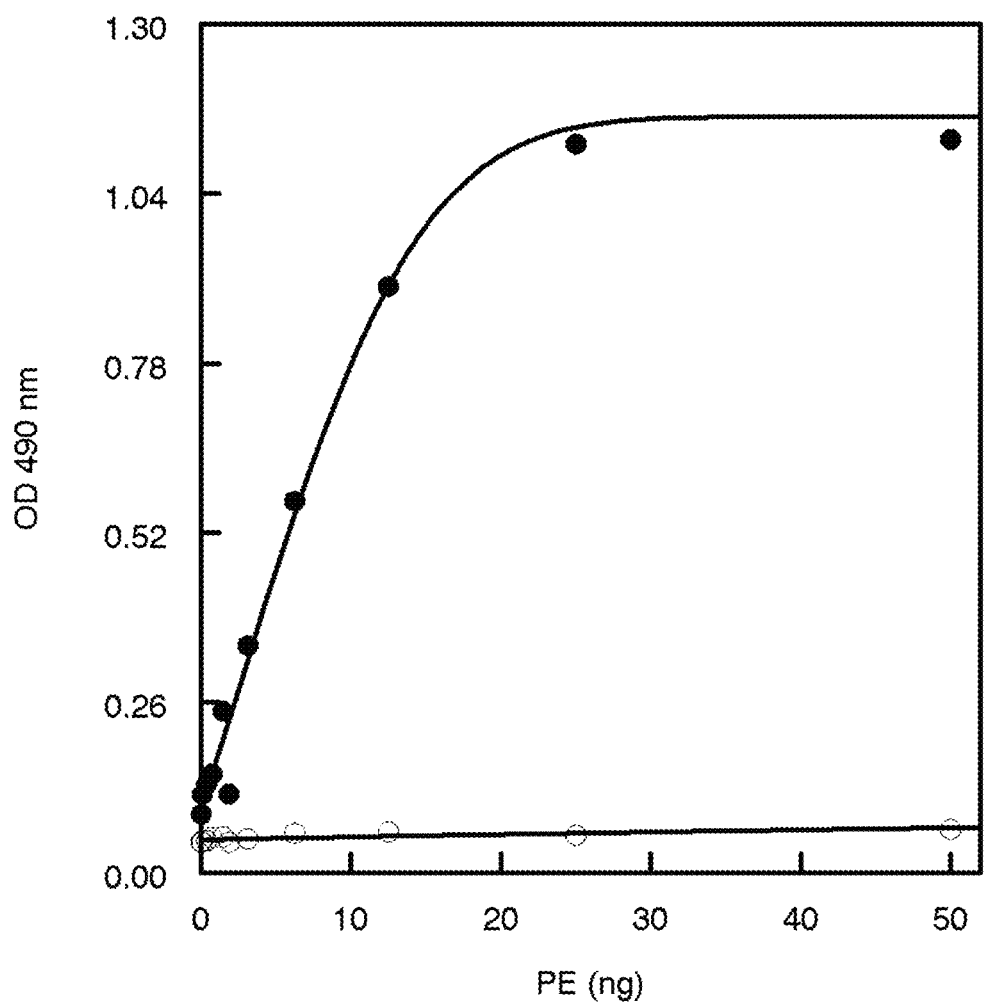
FIG. 9. Specific binding of heparin to phosphatidylethanolamine (PE). ELISA plates were coated with 1 µg heparin sulphate. After washing and blocking with 2% bovine serum albumin the wells were incubated with increasing amounts of LUV containing PE (50 mol % in PC) or PS (50 mol % in PC) for 1 hr. After an additional wash the plate was developed with HRP-annexin 5 or HRP-duramycin. Open circles: PS LUV developed with HRP-annexin 5, closed circles PE LUV developed with HRP-duramycin.

The results presented in FIG. 9 show that heparin binds in a highly selective manner to PE (a pan-exosome marker) but not to PS (the tumor-specific marker). These data indicate that appropriately-labeled heparin can be used to quantify the amount of tumor exosomes bound to a PS-binding ELISA plate or PS-binding latex beads for FACS analysis.

Example 6

Figure 10:
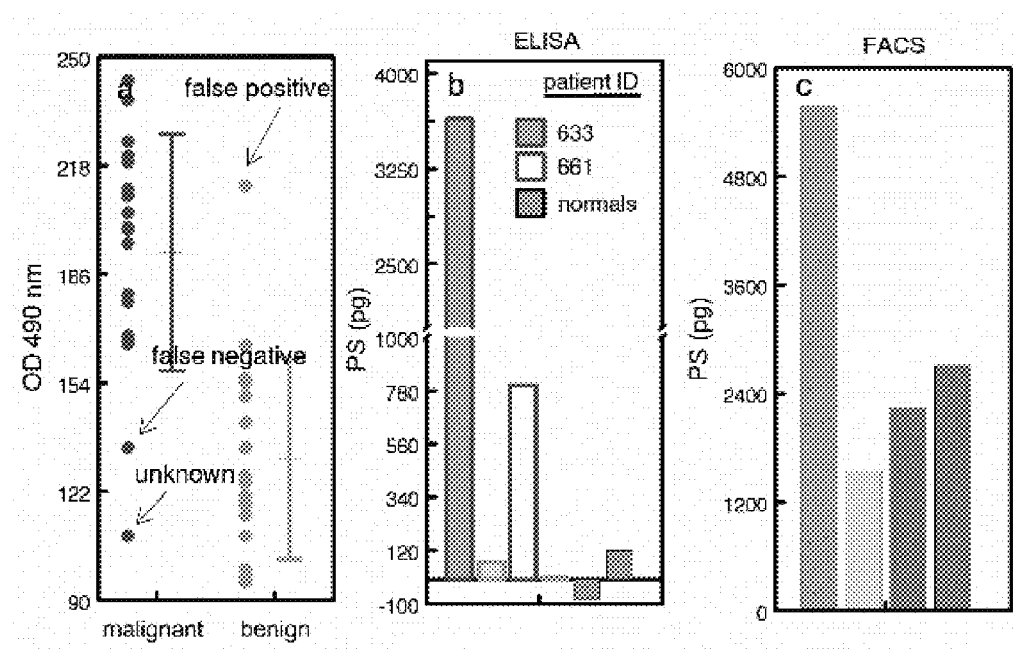
(FIG. 10) Combined ELISA data (a blinded study) from two cohorts of ovarian carcinoma patients with malignant (red) and benign (green) tumors using KL5C betabody capture.
Figure 11:
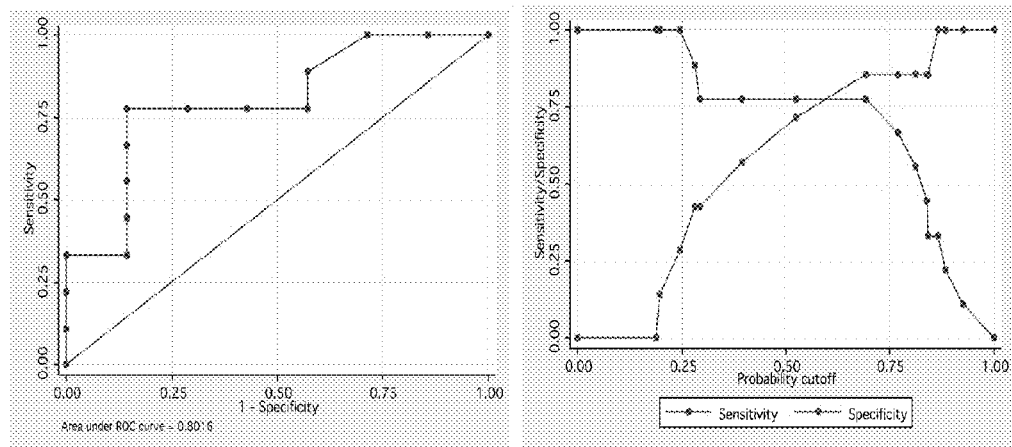
FIG. 11. Receiver operating characteristic (ROC) analysis for predictive accuracy of data shown in FIG. 10A.

Detection of PS-Expressing Tumor Exosomes in Ovarian Carcinoma Patients Before and after Therapeutic Intervention Thirty-five patient plasma samples, all of which were from individuals with suspicious ovarian masses, were tested for tumor exosomes prior to any surgical diagnostic procedures using 1N11-T capture (without additional exogenous β2GP1) and HRP-annexin 5 quantitation. The results in FIG. 10A show two distinct data clusters corresponding to patents with confirmed malignant (red) and benign (green) tumors. With one false positive (this person was a breast cancer patient albeit with a benign ovarian lesion) and one false negative, the patients with malignancies and benign tumors were well separated with means±SD of 192.4±34.8 and 131.7±9.6, respectively. Two sample t-test of the first cohort of 16 patients showed the malignant group had a significantly higher marker value than the benign group (mean 0.189 vs. 0.132, p=0.012) (FIG. 11). ROC analysis of predictive accuracy revealed an AUC of 0.802, with an optimal cutoff of 0.154, and corresponding sensitivity of 0.778 and specificity=0.857 (FIG. 11).

In principle, patients post therapy and in complete remission should have a significant reduction in their levels of circulating PS-positive tumor exosomes. Indeed, analysis of patients by both ELISA (FIG. 10B) and FACS (FIG. 10C) assay ~six months' post-therapy revealed a significant decrease in tumor exosome levels that were well within the range of normal tumor-free individuals. Red, pre-therapy; green, post-therapy; gray, normal plasma from tumor-free individuals.

Example 7

Detection of PS-Expressing Tumor Exosomes in Lung Cancer Patients

Figure 12:
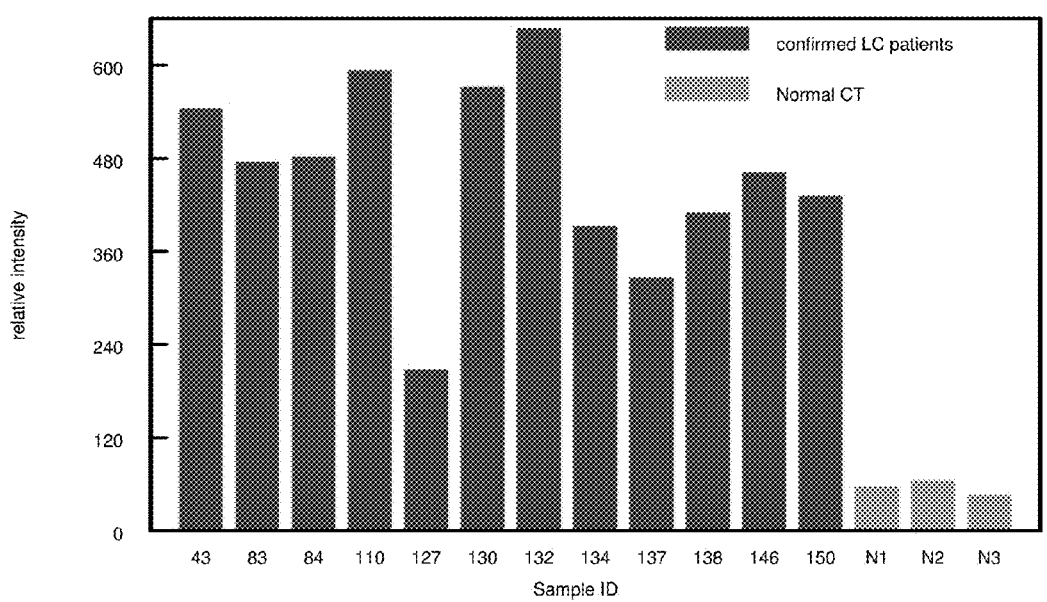
FIG. 12. Assessment of tumor exosomes in lung cancer patients. FACS analysis of tumor exosome levels (a blinded study) in the plasma of lung cancer patients (red) compared to plasma from normal, tumor-free individuals (green).

Analysis by FACS using 1N11-T capture and FITC-annexin 5 detection revealed a ~10-20-fold increase in the expression of PS from exosomes recovered from the plasma of confirmed lung cancer patients vs plasma obtained from normal individuals (FIG. 12).

Example 8

Detection of PS-Expressing Tumor Exosomes in Normal, Tumor-Free Individuals Vs Lung Cancer Patients Normal individuals, To determine "normal" levels of PS-exosomes in plasma of cancer-free individuals, plasma from 10 donors was compared to two OBGYN patients with confirmed malignancies (HGSC and granulosa cell) by both ELISA and FACS assays using 1N11-T capture (without the addition of exogenous β2GP1) and HRP-annexin 5 and FITC-annexin 5 detection, respectively. The data in FIG. 13 show highly consistent differences between the levels of PS-positive exosomes in the plasma of 10 normal individuals' vs both cancer patients. These data confirm that normal tumor-free individuals have virtually no PS-expressing exosomes in the peripheral circulation.

Example 9

Effect of Calcium of β2GP1-Dependent Binding to PS

To exemplify the well-known inhibitory effect of $Ca^{2+}$ on the binding of β2GP1 to PS, binding curves were generated in the presence and absence of $Ca^{2+}$ and in buffer with EDTA chelated $Ca^{2+}$ (FIG. 14). The Figure shows ~50% inhibition of binding in the presence of 5 mM $Ca^{2+}$ that was significantly reversed in the presence of equimolar concentrations of EDTA. These data demonstrate the importance of using $Ca^{2+}$-chelated plasma for the quantitation of PS-expressing tumor exosomes.

Example 10

Discussion

The objective of this study is to develop and validate the utility, accuracy and specificity of a method to quantify tumor-exosomes that are released from tumors to the peripheral blood. The data disclosed above support the use of a highly novel method to detect phosphatidylserine (PS)-expressing tumor-derived exosomes as a cancer-specific blood-based biomarker.

To confirm preliminary tissue culture and clinical data, additional studies will be conducted on blinded blood samples obtained from normal individuals and patients with malignant and benign masses. Upon completion of a series of analyses, patient clinical status at the time of blood collection will be unblinded and compared to the data obtained from the tumor exosome detection assays.

The assay is based on observations indicating that: 1) in contrast to normal cells, exosomes released from tumor cells express PS on the exosome surface making it accessible to PS binding agents (Table 2); 2) tumor cells secrete significantly larger quantities of exosomes than do normal cells; and 3) there is a direct relationship between the concentration of blood borne exosomes and tumor size. The availability of this tool would 1) provide a diagnostic marker that dramatically improves the early detection of cancer; 2) predict whether a tumor is benign or malignant; and 3) provide a predictive marker for response to therapy. Importantly, such a highly accurate diagnostic test for the early detection of tumor exosomes in blood could detect cancer early thereby significantly improving patient survival.

TABLE 2

TUMOR/NORMAL EXOSOME SAMPLES USED FOR PS ANALYSIS

|  | Tumor cell types confirmed to secrete PS-expressing exosomes | Normal cell types confirmed to secrete exosomes that do not express PS |
| --- | --- | --- |
| Mouse lines | B16 melanoma K1735 melanoma C4 melanoma 4T1 breast TRAMP prostate | 3T3 cells |
| Human lines | HCC1833 lung HCC4017 lung HCC4018 lung HCC5032 ovarian | Mesothelial cells HBEC |
| Blood samples | Cancer patient blood | Normal blood |

All of the compositions and/or methods disclosed and claimed herein can be made and executed without undue experimentation in light of the present disclosure. While the compositions and methods of this disclosure have been described in terms of particular embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

PCT No. PCT/US15/18183
U.S. Pat. No. 4,196,265
U.S. Pat. No. 4,472,509
U.S. Pat. No. 4,938,948
U.S. Pat. No. 5,021,236
U.S. Pat. No. 5,563,250
U.S. Pat. No. 8,901,284
U.S. Ser. No. 14/634,607
U.S. Pat. No. 4,680,338
US 2013/0052647 A1
U.S. Pat. No. 5,141,649
WO/2015/085096
Aharon & Brenner, "Microparticles, thrombosis and cancer", Best Practice & Research Clinical Haematology, 22:61-69, 2009.
Al Nedawi et al., "Mast cell-derived exosomes activate endothelial cells to secrete plasminogen activator inhibitor type 1", Arterioscler. Thromb. Vasc. Biol., 25: 1744-1749, 2005.
Andre et al., "Exosomes as potent cell-free peptide-based vaccine. I. Dendritic cell-derived exosomes transfer functional MHC class I/peptide complexes to dendritic cells", J Immunol., 172:2126-2136, 2004.
Andreola et al., "Induction of lymphocyte apoptosis by tumor cell secretion of FasL-bearing microvesicles", J Exp. Med., 195:1303-1316, 2002.
Balasubramanian and Schroit, "Aminophospholipid asymmetry: A matter of life and death," Ann. Rev. Physiol. 65:701-34, 2003.
Brownlee et al., "A Novel "Salting-Out" Procedure for the Isolation of Tumor-Derived Exosomes", J Immunol. Meth., 407: 120-126, 2014.
Chaput et al., "The potential of exosomes in immunotherapy", Expert. Opin. Biol. Ther., 5:737-747, 2005.
Combes et al., A new flow cytometry method of platelet-derived microvesicle quantitation in plasma, Thromb. Haemost., 77:220, 1997.
Duijvesz et al., Proteomic profiling of exosomes leads to the identification of novel biomarkers for prostate cancer. PLoS. One. 8, e82589. PM:24391718, 2013.
Gyorgy et al., "Membrane vesicles, current state-of-the-art: emerging role of extracellular vesicles", Cell. Mo!. Life Sci., 68:2667-2688, 2011.
Huber et al., "Human colorectal cancer cells induce T-cell death through release of proapoptotic microvesicles: role in immune escape", Gastroenterology, 128:1796-1804, 2005.
Iero et al., "Tumour-released exosomes and their implications m cancer immunity", Cell Death. Differ., 15:80-88, 2008.
Im et al., "Label-free detection and molecular profiling of exosomes with a nano-plasmonic sensor", Nature Biotechnology, 32(5):490, 2014; doi: 10.1038/nbt.2886.
Kanwar et al., "Microfluidic device (ExoChip) for On-Chip isolation, quantification and characterization of circulating exosomes", Lab Chip., 14(11):1891-1900, 2014.
Keller et al., "Systemic presence and tumor-growth promoting effect of ovarian carcinoma released exosomes", Cancer Lett., 278:73-81, 2009.
Keller et al., Systemic presence and tumor-growth promoting effect of ovarian carcinoma released exosomes. Cancer Lett. 278, 73-81. PM:19188015, 2009.
Khan et al., Plasma-derived exosomal survivin, a plausible biomarker for early detection of prostate cancer. PLoS. One. 7, e46737. PM:23091600, 2012.
Kim et al., "Fas ligand-positive membranous vesicles isolated from sera of patients with oral cancer induce apoptosis of activated T lymphocytes", Clin. Cancer Res., 11:1010-1020, 2005.
Logozzi et al., High levels of exosomes expressing CD63 and caveolin-1 in plasma of melanoma patients. PLoS. One. 4, e5219. PM:19381331, 2009.
Losche et al., Platelet-derived microvesicles transfer tissue factor to monocytes but not to neutrophils, Platelets, 15:109-115, 2004.
Mesri & Altieri, Endothelial cell activation by leukocyte microparticles, J. Immunol., 161:4382-4387, 1998.
Mitchell et al., Circulating microRNAs as stable blood-based markers for cancer detection. Proc. Natl. Acad. Sci. U.S.A 105, 10513-8. PM:18663219, 2008.
Morel et al., Cellular microparticles: a disseminated storage pool of bioactive vascular effectors, Curr. Opin. Hematol., 11:156-164, 2004.
Noerholm et al., RNA expression patterns in serum microvesicles from patients with glioblastoma multiforme and controls. BMC. Cancer 12, 22 PM:22251860, 2012.
Parolini et al., "Microenvironmental pH is a key factor for exosome traffic in tumor cells'" J. Biol. Chem., 284: 34211-34222, 2009.
Peinado et al., Melanoma exosomes educate bone marrow progenitor cells toward a pro-metastatic phenotype through MET. Nat. Med. 18, 883-91. PM:22635005, 2012.
Rabinowits et al., Exosomal microRNA: a diagnostic marker for lung cancer. Clin. Lung Cancer 10, 42-6. PM:19289371, 2009.
Silva et al., Vesicle-related microRNAs in plasma of nonsmall cell lung cancer patients and correlation with survival. Eur. Respir. J. 37, 617-23. PM:20595154, 2011.
Simpson and Mathivanan, "Extracellular Microvesicles: The Need for Internationally Recognised Nomenclature and Stringent Purification Criteria", J. Proteomics Bioinform., 5:2 http://dx.doi.org/10.4172/jpb.lOOOOelO, 2012.
Smalley et al., Isolation and identification of potential urinary microparticle biomarkers of bladder cancer. J. Proteome. Res 7, 2088-96. PM:18373357, 2008.
Szajnik et al., "Tumor-derived microvesicles induce, expand and up-regulate biological activities of human regulatory T cells (Treg)", PLoS One, 5:el 1469, 2010.
Taylor & Gercel-Taylor, MicroRNA signatures of tumor-derived exosomes as diagnostic biomarkers of ovarian cancer. Gynecol. Oncol. 110, 13-21. PM:18589210, 2008.
Taylor and Gercel-Taylor, "MicroRNA signatures of tumor-derived exosomes as diagnostic biomarkers of ovarian cancer", Gynecol. Oncol., 110:13-21, 2008.
Thery et al., "Exosomes: composition, biogenesis and function", Nat. Rev. Immunol., 2:569-579, 2002.
Thery et al., "Isolation and characterization of exosomes from cell culture supernatants and biological fluids", Curr. Protoc. Cell Biol., Chapter 3:Unit, 2006.
Thery et al., "Membrane vesicles as conveyors of immune responses", Nat. Rev. Immunol., 9:581-593, 2009.
Thomas et al., Exosomal Proteome Profiling: A Potential Multi-Marker Cellular Phenotyping Tool to Characterize Hypoxia-Induced Radiation Resistance in Breast Cancer. Proteomes. 1, 87-108. PM:24860738, 2013.
Thorpe & Wawrzynczak, Cancer Res. 47(22):5924-31, 1987.
Valenti et al., "Tumor-released microvesicles as vehicles of immunosuppression", Cancer Res., 67:2912-2915, 2007.

Wieckowski et al., "Tumor-derived microvesicles promote regulatory T cell expansion and induce apoptosis in tumor-reactive activated CDS+ T lymphocytes", J Immunol., 183:3720-3730, 2009.

What is claimed:

1. A method of detecting a cancer cell-derived exosome from a subject comprising:
   (a) providing a sample from said subject;
   (b) contacting said sample with phosphatidylserine (PS) binding agent or agents, wherein said binding agent comprises a β2GP1 PS-binding domain; and
   (c) detecting binding of said binding agent to PS expressed on the outer leaflet of the particle membrane of said exosome, thereby detecting said exosome.

2. The method of claim 1, wherein said sample is a fluid.

3. The method of claim 2, wherein said fluid is blood, serum, plasma, sputum, urine, saliva or tears.

4. The method of claim 1, wherein said PS binding agent or agents exhibits increased binding to PS in the absence of calcium, as compared to binding to PS in the presence of calcium.

5. The method of claim 1, wherein the sample is essentially free of available calcium or unchelated calcium.

6. The method of claim 1, wherein said PS binding agent or agents is/are bound directly or indirectly to a support.

7. The method of claim 6, wherein said PS binding agent or agents is bound to said support indirectly through an antibody.

8. The method of claim 7, wherein said antibody is monomeric, dimeric or tetrameric.

9. The method of claim 1, wherein detecting comprises contacting the sample of step (b) with an exosome binding agent.

10. The method of claim 1, wherein detecting is quantitative.

11. The method of claim 1, wherein said cancer cell-derived exosome is from a lung cancer cell, a pancreatic cancer cell, an ovarian cancer cell, a colon cancer cell, a renal cancer cell, a liver cancer cell, a skin cancer cell, a brain cancer cell, a head and neck cancer cell, or a thyroid cancer cell.

12. The method of claim 1, further comprising enriching, concentrating or purifying exosomes prior to step (b).

13. The method of claim 1, wherein the subject is a human or a non-human mammal.

14. The method of claim 1, further comprising administering a cancer therapy to said subject.

* * * * *